United States Patent
Tas et al.

(10) Patent No.: US 8,312,772 B2
(45) Date of Patent: Nov. 20, 2012

(54) CHARACTERIZATION WITH PICOSECOND ULTRASONICS OF METAL PORTIONS OF SAMPLES POTENTIALLY SUBJECT TO EROSION

(75) Inventors: Guray Tas, Flanders, NJ (US); Sean P. Leary, Saraburi (TH); Dario Alliata, Viterbo (IT); Jana Clerico, Stanhope, NJ (US); Priya Mukundhan, Lake Hopatcong, NJ (US); Zhongning Dai, Bridgewater, NJ (US)

(73) Assignee: Rudolph Technologies, Inc., Flanders, NJ (US)

(*) Notice: Subject to any disclaimer, the term of this patent is extended or adjusted under 35 U.S.C. 154(b) by 143 days.

(21) Appl. No.: 12/449,837

(22) PCT Filed: Feb. 28, 2008

(86) PCT No.: PCT/US2008/002649
§ 371 (c)(1),
(2), (4) Date: Jul. 13, 2010

(87) PCT Pub. No.: WO2008/106199
PCT Pub. Date: Sep. 4, 2008

(65) Prior Publication Data
US 2010/0281981 A1  Nov. 11, 2010

(51) Int. Cl.
 *G01N 29/24* (2006.01)
 *G01N 21/00* (2006.01)
(52) U.S. Cl. .......................... 73/627; 356/432
(58) Field of Classification Search ............ 73/627–629, 73/618–620, 642–643, 655–657; 356/502–503, 356/432, 445; 359/302, 247, 290
See application file for complete search history.

(56) References Cited

U.S. PATENT DOCUMENTS

| | | | | |
|---|---|---|---|---|
| 5,748,318 | A |  5/1998 | Maris et al. | 356/630 |
| 5,844,684 | A * | 12/1998 | Maris et al. | 356/432 |
| 6,552,803 | B1 * |  4/2003 | Wang et al. | 356/503 |
| 2004/0085540 | A1 * |  5/2004 | Lapotko et al. | 356/432 |
| 2005/0023434 | A1 * |  2/2005 | Yacoubian | 250/200 |
| 2005/0095730 | A1 |  5/2005 | Mikami | 438/16 |
| 2006/0215175 | A1 * |  9/2006 | Yacoubian | 356/502 |
| 2006/0256916 | A1 * | 11/2006 | Kotelyanskii et al. | 378/71 |
| 2006/0272419 | A1 * | 12/2006 | Maris et al. | 73/606 |

FOREIGN PATENT DOCUMENTS
WO  WO-99/44052 A1  9/1999
WO  WO-99/56077 A1  11/1999

OTHER PUBLICATIONS

Stoner, Robert J., et al., "Picosecond Ultrasonics: A New Approach for Control of Thin Metal Processes", © 1998 The American Institute of Physics, pp. 385-394.

* cited by examiner

*Primary Examiner* — Helen C. Kwok
(74) *Attorney, Agent, or Firm* — Harrington & Smith

(57) ABSTRACT

A method for evaluating a manufacturing process is described. The method includes generating an optical pump beam pulse and directing the optical pump beam pulse to a surface of a sample. A probe pulse is generated and directed the probe pulse to the surface of the sample. A probe pulse response signal is detected. A change in the probe pulse varying in response to the acoustic signal forms the probe pulse response signal. An evaluation of one or more manufacturing process steps used to create the sample is made based upon the probe pulse response signal. Additionally the method may be used for process control of a CMP process. Apparatus are also described.

20 Claims, 21 Drawing Sheets

FIB-SEM

CHARACTERIZATION WITH PICOSECOND ULTRASONICS OF METAL PORTIONS OF SAMPLES POTENTIALLY SUBJECT TO EROSION

TECHNICAL FIELD

This invention relates generally to measuring semiconductor materials and, more specifically, relates to measuring metal line arrays and layers.

BACKGROUND

Chemical mechanical planarization (CMP) is a critical process for creating high performance and high yield interconnected structures on integrated circuits (IC) with, e.g., copper interconnects.

CMP polishing rates are dependent on many variables including the electroplate profile, slurry chemistry, pad wear, inter-level dielectric material and pattern density. These effects become more pronounced at advanced technology nodes, where CMP dishing and erosion may have a significant impact on the resistance of the interconnect structures.

If line structures are under polished, residual copper or barrier will short out the circuitry resulting in defective dies. However, over polishing increases the line resistance, negatively impacting both the speed and performance of chips.

To maintain the specified interconnect resistance, it is important to monitor the copper thickness of both bond pads and line array structures. These thicknesses may vary significantly across the wafer and from wafer to wafer, so a high-throughput inline metrology technique is desirable.

To maintain high yield, it is thus critical to maintain the copper lines at the desired thickness. This requires strict process control.

Several metrology techniques are used to monitor CMP processes including scanning electron microscopy (SEM) and optical techniques that measure dielectric polishing and high resolution profilometers that can measure the relative height differences between structures such as interlayer dielectric pads, copper pads, and line arrays.

Nonetheless, such metrology techniques could be improved when measuring line arrays and layers made of metals such as copper.

BRIEF SUMMARY

An exemplary embodiment in accordance with this invention is a method for evaluating a manufacturing process. The method includes generating an optical pump beam pulse and directing the optical pump beam pulse to a surface of a sample. A probe pulse is generated and directed the probe pulse to the surface of the sample. A probe pulse response signal is detected. A change in the probe pulse varying in response to the acoustic signal forms the probe pulse response signal. An evaluation of one or more manufacturing process steps used to create the sample is made based upon the probe pulse response signal.

Another exemplary embodiment in accordance with this invention is an apparatus for evaluating a manufacturing process. The apparatus includes a light source configured to generate an optical pump beam pulse, to direct the optical pump beam pulse to a surface of a sample to generate an acoustic signal, to generate a probe pulse and to direct the probe pulse to the surface of the sample. A detector is included to detect a probe pulse response signal. The probe pulse response signal is formed based on a change in the probe pulse varying in response to the acoustic signal. A processing unit, which can generate an evaluation of one or more manufacturing process steps used to create the sample based upon the probe pulse response signal, is also included.

A further exemplary embodiment in accordance with this invention is an apparatus for evaluating a manufacturing process. The apparatus includes a first means for generating an optical pump beam pulse and directing the optical pump beam pulse to a surface of a sample. A second means for generating a probe pulse and directing the probe pulse to the surface of the sample is included. The apparatus includes a means for detecting a probe pulse response signal. A change in the probe pulse varying in response to the acoustic signal forms the probe pulse response signal. An evaluation means for generating an evaluation of at least one manufacturing process step used to create the sample based upon the probe pulse response signal is included.

BRIEF DESCRIPTION OF THE DRAWINGS

The foregoing and other aspects of embodiments of this invention are made more evident in the following Detailed Description of Exemplary Embodiments, when read in conjunction with the attached Drawing Figures, wherein:

FIG. 19, including FIG. 19A shows bond pad results with correlation ($R^2$) of 0.90, and FIG. 19B shows the line array results with correlation of 0.95;

DETAILED DESCRIPTION OF EXEMPLARY EMBODIMENTS

Figure 1:
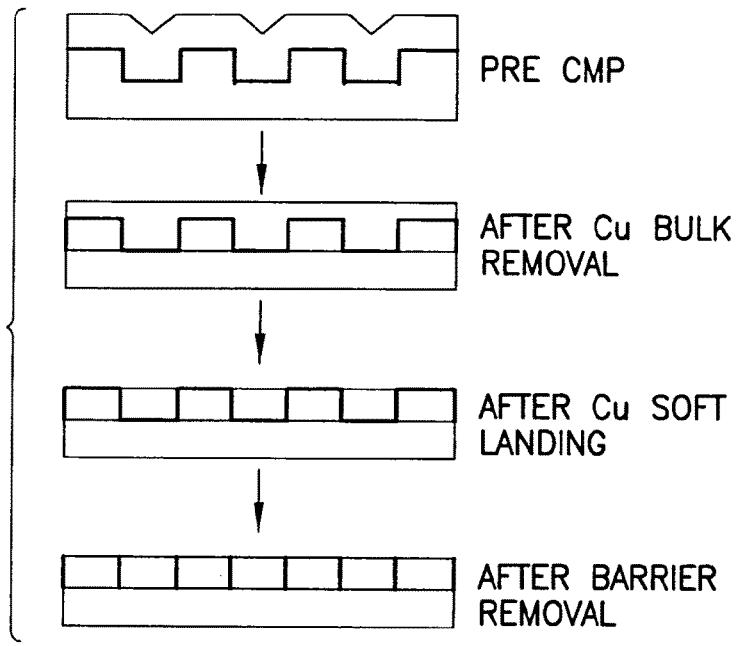
FIG. 1 is an example of copper CMP process.

As noted above, chemical mechanical polishing (CMP) is a critical process step for producing high performance and high yield integrated circuits (IC) with, e.g., copper interconnects. Several metrology techniques are used to monitor CMP processes including optical techniques that measure dielectric polishing and high resolution profilometers that can measure the relative height differences between structures such as interlayer dielectric pads, copper pads, and line arrays.

In contrast, the picosecond ultrasonic method measures the copper thickness and therefore directly measures a parameter (e.g., characteristic) of interest for CMP process monitoring.

The picosecond ultrasonic technique is well established for measuring on solid copper structures such as pads. However, in the dense narrow line arrays that are required for current and next generation devices, the measurement spot size, while only approximately 10 μm in diameter, may cover hundreds of copper line/dielectric pairs. Therefore new detection apparatus and methods were developed that are, in an exemplary embodiment, insensitive to the dielectric signal. The capabilities of picosecond ultrasonic to measure on both copper pads and 0.6 μm line arrays were tested. The results were compared against Scanning Electron Microscopy (SEM). The samples included different products and six different metal layers. The picosecond ultrasonic system and method are described herein, and detailed results presented for various samples.

The picosecond ultrasonic metrology technique has been implemented for CMP monitoring at the 90 nm technology node and is being qualified for 65 nm processes. Picosecond ultrasonics is a non-contact, nondestructive technique that uses, e.g., an ultrafast laser light pulse to generate a sound wave in the top layer film on the tested areas. This sound wave travels into the structure until it meets an interface. At the interface an echo is generated. The echo then travels back to the surface, where it is detected. A characteristic (e.g., the thickness) of the film can therefore be determined by multiplying the one-way trip time of the echo through the film and the speed of sound in the material. This technique has been extensively used to characterize various metal films, including the sub-micron line array structures used as CMP test structures. Described herein are picosecond ultrasonic techniques and their applications for characterizing, e.g., CMP processes.

For ease of reference, this description is separated in to a number of different sections.

I. Introduction

As the feature size of semiconductor devices continues to shrink down, the transistor switching speed has been greatly improved. On the other hand, the demand for high-density integration drives the interconnect dimensions to decrease, and the number of metal layers to increase, resulting in an increase of interconnect resistance and as well parasitic capacitance. See, e.g., L. He, A. B. Kahng, K. H. Tam, and J. Xiong, "Variability-Driven Considerations in the Design of Integrated-Circuit Global Interconnects", Proc 21th VMIC, 214-221, September, 2004. To reduce interconnect resistance, Cu interconnects have been implemented. See, e.g., R. H. Havemann and J. A. Hutchby, "High Performance Interconnects: An Integration Overview", Proceedings of the IEEE, Vol. 89, No. 5, May 2001.

Cu interconnects are normally fabricated by using the dual damascene approach. Unlike traditional metallization of aluminum, where aluminum is deposited on top of inter-level dielectric (ILD), patterned, and etched, copper metallization requires a damascene process, because copper is more difficult to etch. In the damascene process, ILD is first deposited and patterned to define trenches, where the metal lines will lie. Metal is then deposited to fill the patterned oxide trenches, and polished to remove the excess metal outside the desired lines using CMP. Getting CMP right is one of the key factors in successful back-end of line manufacturing.

An optimized copper removal process requires a proper balance between bulk removal and clearing steps. A goal is to eliminate end point failure, which results in over-polished or scrapped wafers, and to have tighter process control, limiting yield loss.

Copper damascene structure polishing is usually achieved by means of three steps performed on three different platens (see FIG. 1): step 1 is bulk copper removal, step 2 is device clearing often referred to as 'soft landing', step 3 is barrier removal and oxide buffing. To obtain good device functionality, it is essential to avoid having any structure be over-polished or under-polished.

Figure 2:
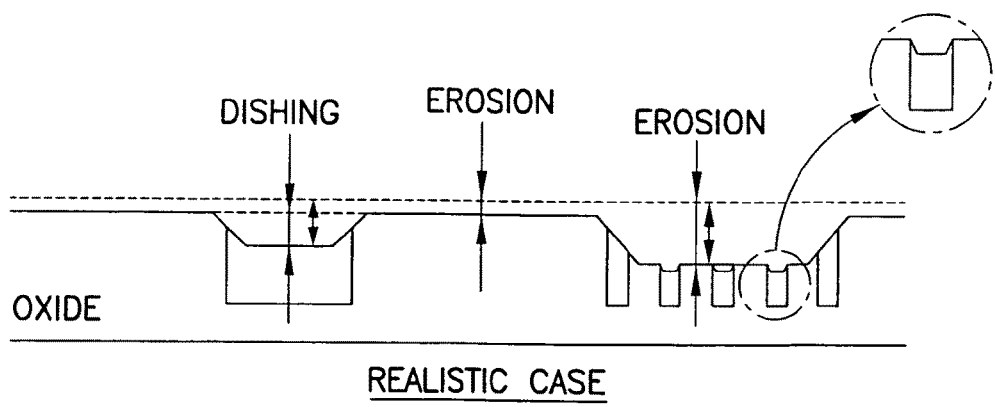
FIG. 2 is an example of dishing and erosion.

Within Cu CMP operation, the device clearing (step 2 as shown in FIG. 1) is a challenging step since it is preferred that no copper residues are to be left whatever the design calls for interconnects, whereas minimal topography should be generated. Ideally, the polished copper should be perfectly flat. Unfortunately, copper lines suffer from dishing and erosion due to CMP; see FIG. 2.

Dishing is defined as the recessed height of a copper line compared to the neighboring oxide. Erosion is defined as the difference between the original oxide height and the post polish oxide height. Cu thickness loss is the sum of field oxide loss, local oxide erosion, and copper dishing.

An important factor is to maintain precise control of copper and oxide thickness post CMP.

While global-scale CMP metrology techniques are useful for end pointing the process, they cannot offer characterization of the nanotopography variations that can have a significant impact on final chip performance. See, e.g., T. Park. et al., "Overview of Methods for Characterization of Pattern Dependencies in Copper CMP", Proc. CMPMIC, pp. 196-205, March 2000. Surface profilometry can determine topography and the planarity for future process steps, but cannot directly measure copper line thickness and therefore, surface profilometry may provide inaccurate results when the initial trench depth or erosion of the field areas is not as expected. Electrical tests offer excellent correlation to final device performance, but are relatively slow and generally used offline. This work demonstrates, e.g., the use of picosecond ultrasonics to characterize erosion of 50 percent metal dense line arrays of copper that will be used on 65 nm devices from metal level (ML) 1 to 6.

Rapid device scaling has been the most important factor governing the growth of the semiconductor industry, which has produced integrated circuits (IC) with faster speed and lower power consumption. In order to minimize resistance-capacitance (RC) delays, device manufacturers have transitioned from using aluminum interconnects to copper interconnects and from oxide to low dielectric constant materials. These advances in IC manufacturing have resulted in an increase in the device density up to one billion transistors/$cm^2$; therefore, a corresponding increase in circuit functionality requires many layers of metal interconnects to facilitate the necessary device communication. The ability to effectively and efficiently planarize the metal and dielectric layers which are used to insulate these complex interconnect levels is highly important for realizing the performance of these devices.

Chemical mechanical polishing (CMP) has emerged as the most widely used method for achieving planarization in copper damascene structures. CMP has become one of the critical process steps for producing high performance, high yield devices.

Key metrics for Copper CMP are dishing and erosion topography, post-polish defectivity, integration capability and cost-effectiveness. See, e.g., C. L. Borst, S. M. Smith and M. Eissa, "Challenges and Rewards of Low-abrasive copper CMP: Evaluation and Integration for Single Damascene Cu/Low-k Interconnects for the 90 µm Node," MRS Symposium Proceedings, pp 3-14, April 2004. Substantial copper dishing/erosion results in copper loss in the lines leading to increase in the sheet resistance and undesired topography. Metal thickness loss caused by dishing exhibits strong correlation with metal line width. For example, bond pads and wide lines show more dishing than sub-micron line array structures. As a result, depending on the die layout, copper thickness distribution across a wafer could vary widely.

Also, copper loss due to dishing has a direct impact on the depth of focus margin of subsequent photo-lithography steps. As critical dimensions shrink, photo-lithography tools continue to reduce the depth of focus. Devices may use five to 15 subsequent litho steps for a given interconnect build and hence improved topography margin for focus and patterning is increasingly important and places stringent requirements on the Cu CMP process. See C. L. Borst et al.

Achieving planarity on product wafers is challenging because both electroplate and CMP processes are strongly pattern dependent. The rate of copper plating is affected by line width, the spacing between lines, and interactions with other structures within 5 to 10 µm. See, e.g., T. Park, T. Tubgawa, and D. Boning, "Pattern Dependent Modeling of Electroplated Copper Profiles", International Interconnect Technology Conference, pp. 274-276, June 2001.

Therefore, the copper overburden may exhibit non-uniform topography, as well as larger scale non-uniformities resulting from electrode placement and electrolyte distribution. The CMP process, then, begins with a non-planar surface and proceeds to polish at a rate that is inversely proportional to effective pattern density. See, e.g., D. Boning, B. Lee, T. Tubawa, and T. Park, "Models for Pattern Dependencies: Capturing Effects in Oxide, STI, and Copper CMP", Semicon/West Technical Symposium: CMP Technology for ULSI Manufacturing, Jul. 17, 2001.

Once the barrier has been cleared, distinct differences in the polishing rate can be observed when the pattern density varies over a 50 to 200 µm range, and short-range dependencies can impact the polishing rate of individual lines or spacers. See, e.g., T. Park. et. al, "Overview of Methods for Characterization of Pattern Dependencies in Copper CMP", Proc. CMP-MIC, pp. 196-205, March 2000. In addition to pattern dependent effects, the polishing rate is affected by factors including pad wear, polish head pressure and slurry changes.

In some cases, using automated process control (APC), it is possible to combine a feed forward model that compensates for incoming wafer variations with a feed backward model that compensates for CMP variations. Examples of APC are shown in U.S. Pat. No. 7,083,495, "Advanced Process Control Approach for Copper Interconnect Wiring Sheet Resistance Control". A copper thickness target can be established for the first wafer and post-CMP measurements from that wafer can be used to modify the polishing rate of subsequent wafers.

Despite these challenges, the basic electroplate and CMP processes are expected to be used through, at least, the 32 nm technology node. See, e.g., M. Hsieh, J. Yeh, M. Tasi, K. Wang, J. Tan, S. Leary, "In-line monitoring of advanced copper chemical mechanical planarization processes with picosecond ultrasonic metrology," Proc. SPIE Vol 6152, 61522C, Metrology, Inspection and Process Control for Microlithography, March 2006 and J. Dukovic, "Copper electroplating, CMP challenges grow more complex at 65-nm node and below", MICRO, Volume 23, Number 6 (October/November 2005.

However, the transition to the 65 nm technology node has added some additional complexity. With shrinking line width, the resistance of the copper begins to increase because the lateral line dimension is in the range of the mean free path of the conduction electrons. See, e.g., W. Steinhogl, G. Schindler, G. Steinlesberger, and M. Engelhardt, "Size-dependent resistivity of metallic wires in the mesoscopic range", Physical Review B, 66, 075414 (2002). This effect can be mitigated by increasing line height (see, e.g., W. Zhang, et. al., "Impact of line height on copper resistivity and interconnect RC delays: a geometry approach to reduce the size effect", Advanced Metallization Conference, September 2005), which can be achieved by minimizing dishing and erosion. Anti-dishing and anti-erosion slurries have been developed to address these concerns.

The second major challenge is the increased use of low-k and ultra low-k dielectric materials that are relatively mechanically weak compared to SiO2, FSG, or even first generation SiCOH materials widely used in the 90 nm node. These materials have different polishing rates and have exhibited a variety of integration problems including delamination, peeling, and cracking. See, e.g., G. Grover, "Copper CMP Faces it Share of Challenges for the Future", Semiconductor Magazine, May 2001.

In future technology nodes, 45 nm and below, process specifications are becoming tighter and there is an increasing need to minimize line width and line height variations within the wafer as well. Hence the necessity to monitor copper thickness at both the die-level and wafer-level becomes important for final chip performance.

Techniques such as surface profilometry are useful to determine the surface topography and planarity for future process steps but fall short as they do not provide direct measurements of copper line thickness. Also, surface profilometry techniques may provide inaccurate results when the initial trench depth or erosion of the open field areas vary unexpectedly. Electrical tests offer excellent correlation to final device performance, but are slow and are generally used off-line.

Optical critical dimension (OCD) measurements have been promoted for measuring both trench depth and width for the 65 nm and lower technology nodes. However, the extendibility of this technology to 45 nm node poses significant challenges. At the lower process nodes, the critical dimensions become very much less than the current minimum measurement wavelength, and simultaneously the line thickness is also expected to be reduced which may limit the usefulness of this method. See, e.g., F. L. Terry Jr., "Accuracy Limitations in Specular-Mode Optical Topography Extraction," Metrology, Inspection, and Process Control for Microlithography XVII, Proceedings of SPIE, Vol 5038 (2003) 547-558.

Picosecond ultrasonics based metrology has been successfully adapted in copper process monitoring starting at the 130 nm through the 65 nm technology nodes. Picosecond ultrasonics is described in, e.g., C. Morath, et. al., "Ultrasonic multi-layer metal film metrology", Solid State Technology, June 1997. Extendibility of this technology to 45 nm node has also been demonstrated. Herein, the use of this technology in the Cu electroplating and CMP areas by providing examples for process monitoring (both die level and wafer level uniformity) as well as excursion detection is discussed. This proven technology provides rapid and gauge-capable measurements allowing within wafer and wafer-to-wafer measurements at production-worthy throughputs.

II. Exemplary Materials and Methods

A. Samples

Samples include 8 inch wafers processed according to the specific product requirement. Target areas for investigation are described as is follows: Cu full sheet ($100\times70$ $\mu m^2$); Arrays of Cu lines 0.6 µm in width, 50% metal density ($100\times70$ $\mu m^2$); and Arrays of Cu lines 10 µm in width, 66% metal density.

B. Picosecond Ultrasonic Detection

Picosecond ultrasonic Laser Sonar (PULSE, trademark, Rudolph Technologies, Inc.) metrology is a non-contact, non-destructive technique that uses laser light to measure thickness and other characteristics of opaque films. Picosecond ultrasonics is a non-contact, nondestructive technique that uses laser light to measure thickness and other physical properties of thin metallic films. Picosecond ultrasonics is described, e.g., in C. Thomsen, H. T. Grahn, H. J. Maris, and J. Tauc, "Surface generation and detection of phonon by picosecond light pulse", Physical Review B, Vol 34, No. 6, pp. 4129-4138, 1986.

Figure 3:
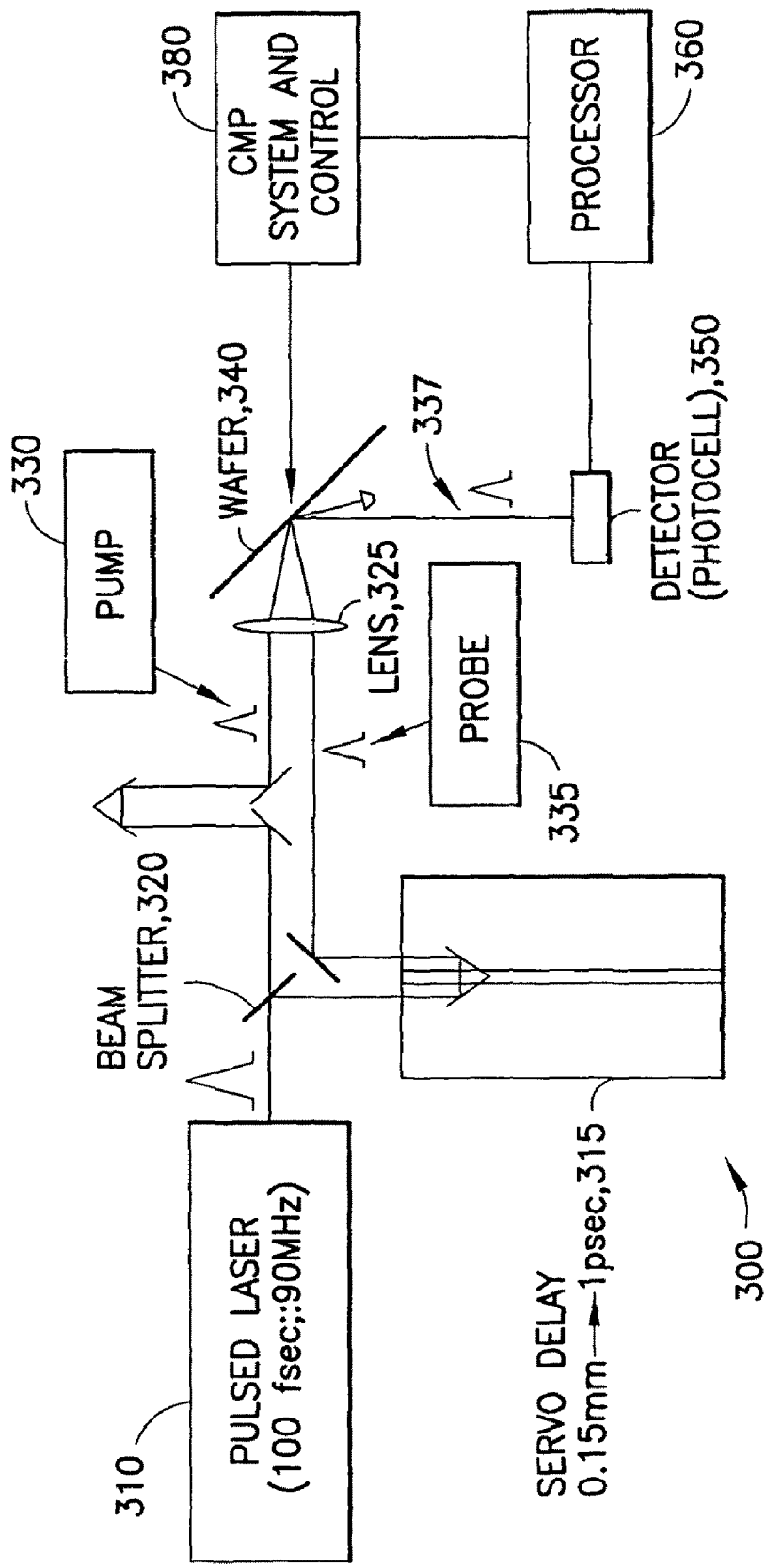
FIG. 3 is simple diagram of a picosecond ultrasonic system for use with the exemplary embodiments of the invention.

See FIG. 3 for a simple diagram of a picosecond ultrasonic system 300 for use with the exemplary embodiments of the invention. The picosecond ultrasonic technique uses a 0.1 psec (picosecond) laser flash to raise the temperature (typically 5 to 10 degrees centigrade, C) of a small region ($5\times7$ µm, micron, area) on the sample's surface. See, e.g., C. Thomsen et al., "Surface generation and detection of phonon by picosecond light pulse", Physical Review B, Vol. 34, No. 6, pp. 4129-4138, 1986. The opaque surface layer absorbs energy from the pump pulse 330, launching a longitudinal strain pulse (e.g., sound wave) that travels down through the multistack at the speed of sound. The strain reflected back by any interface encountered causes a local change, e.g., in the index of refraction.

This change is detected by the probe pulse 335, which has been diverted from the pump pulse 330 (in this non-limiting example, created by the pulsed laser 310; it is also possible to use a second laser to create the probe pulse) by a beam splitter 320. The delay stage, e.g., servo delay 315, varies the time between the pump pulse 330 and probe pulses 335, allowing the changes occurring over a period of time to be detected. The pump pulse 330 and probe pulse 335 may be directed through a lens 325 at the wafer 340. The probe pulse 335 interacts with the film becoming the probe pulse response signal 337, which is detected in the detector 350, e.g., a photocell.

A characteristic of the film on the wafer 340, e.g., the thickness, is then determined, e.g., by the transmission time for a one-way trip through the film multiplied by the speed of sound in the material. The processor 360 is configured to determine the characteristic of the film by using information from the detector 350. In an exemplary embodiment, the processor 360 may also be coupled to a CMP process and control system 380, which uses information from the processor 360 to control the CMP process.

Figure 4:
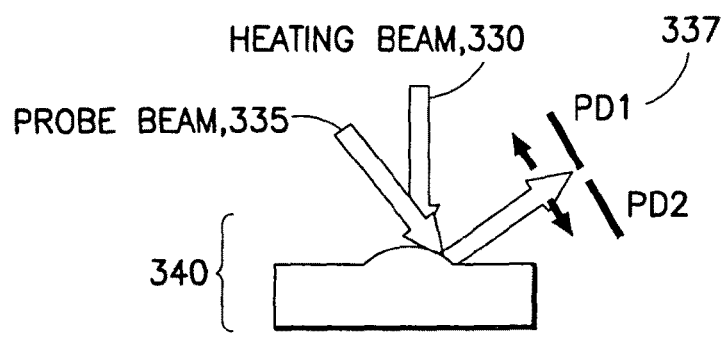
FIG. 4 is a PSD detector scheme, where PD1 and PD2 are the two photodetectors used in the system of FIG. 3 in an exemplary embodiment.

To extend the method to a sub-micron range, a second detection method has been introduced. The echo return causes a slight displacement at the surface of the test site. This displacement then deflects the probe pulse beam 335 and the probe pulse response signal 337 is received at the detector (FIG. 4). A major advantage of this method is its relative insensitivity to the signal from the ILD surrounding the copper lines.

Measurements may be performed by a MetaPULSE-II system (Rudolph Technologies, Inc) (see FIG. 3) equipped with a Position Sensitive Detector (PSD) (see FIG. 4) to measure copper lines at the sub-micron range. It is noted that FIG. 4 shows, as a non-limiting example, two separate sensors; in other embodiments, a single (e.g., position sensitive) sensor might be used.

Figure 5:
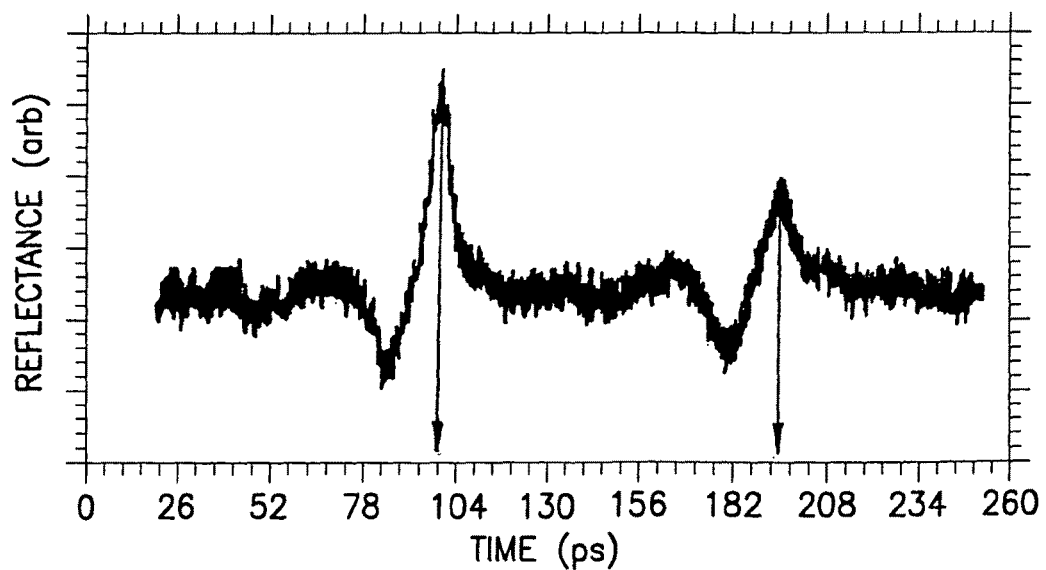
FIG. 5 shows a graph corresponding to an example of a measured signal from a 2400 Å copper film, where film thickness is determined using echo positions, and where 100 ps (picoseconds) for the first round trip and 200 ps second round trip through the film are identified in the figure.

FIG. 5 shows a typical reflectivity signal (e.g., determined by the processor 360 of the system 300 of FIG. 3) from a 2400 Å Cu film. The echo positions are identified in FIG. 5. The first echo returns to the surface at ~100 ps and the second echo arrives at ~200 ps. Thickness of the film is determined using the echo positions as follows:

Thickness=Speed of sound in the material×1/2(round trip time); and

Thickness=48Å/ps×1/2(100ps)=2400Å.

Measurements as seen above can be performed with 5 μm×7 μm laser spot size on bond pad or line array test sites as small as 30 μm×30 μm. A typical measurement time is about 2-3 seconds. This ability of measuring in small test sites, fast throughput and non-destructive nature of the picosecond ultrasonics have qualified the technique as a thickness metrology on product wafers. As a result, picosecond ultrasonics based MetaPULSE metrology tools have been widely used to monitor copper processes.

When measuring sub-micron line arrays, 0.5 μm line width/0.5 μm spacing, the laser spot covers a number of copper lines and inter-level dielectric (ILD) spacings. The resulting response is a superposition of 2D (lateral and vertical) vibration modes and is also further complicated due to convolution of signals from the metal and ILD. In order to simplify the measurements, a position sensitive detection system (PSD) has been developed. Details of measurement using the PSD technique for metal line array measurements are discussed elsewhere. See, e.g., M. Hsieh et al., cited above.

III. Exemplary Results

A. Validation of the Picosecond Ultrasonics Methodology

Picosecond Ultrasonics methodology was validated by characterizing several products through all six copper metallization levels. An example of such characterization is shown in FIG. 6.

Figure 6A:
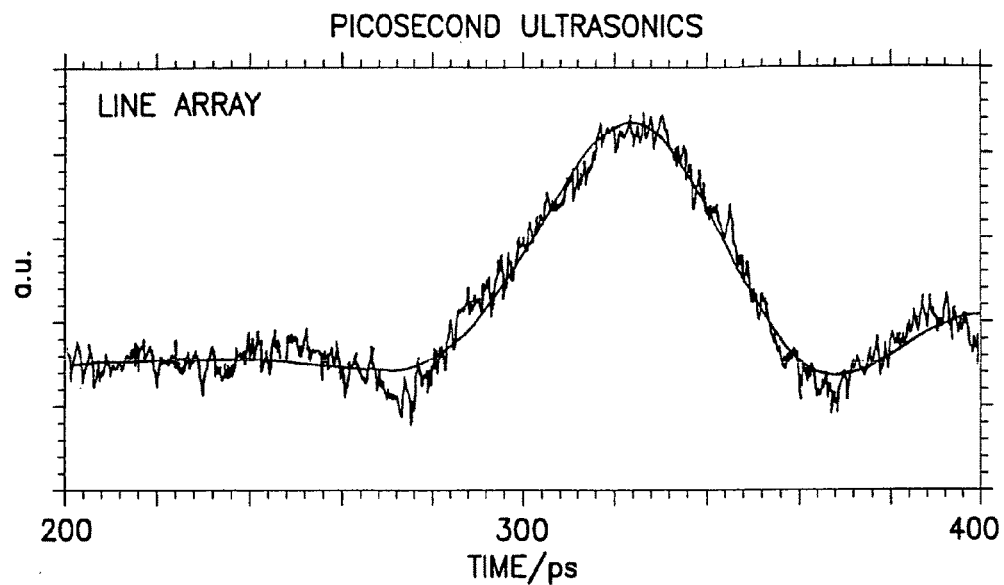
FIG. 6 includes FIGS. 6A-6D, including FIGS. 6A and 6B showing results of picosecond ultrasonics signals for a Cu line array and a Cu full sheet, respectively.
FIGS. 6C and 6D show corresponding cross sections by SEM to FIGS. 6A and 6B, respectively.
Figure 6B:
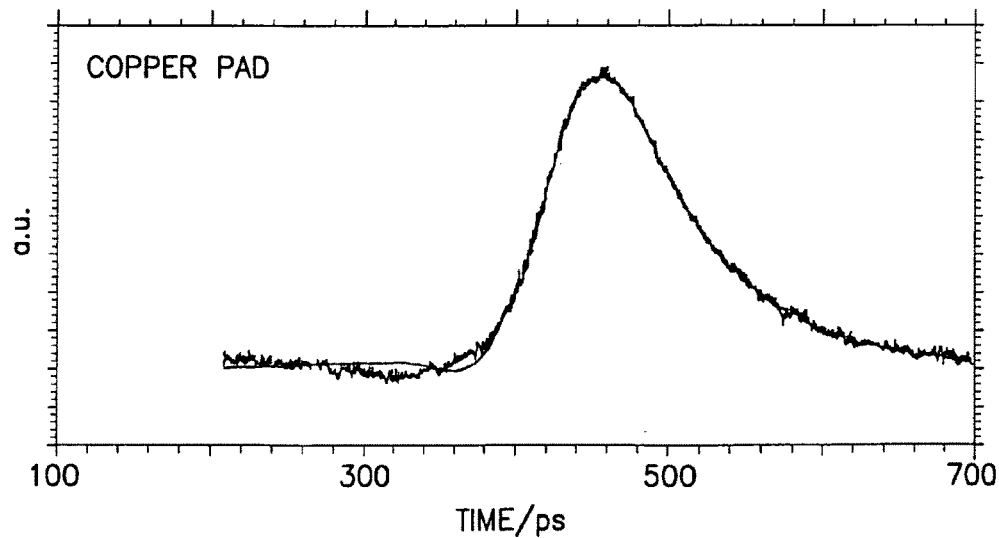
Figure 6C:
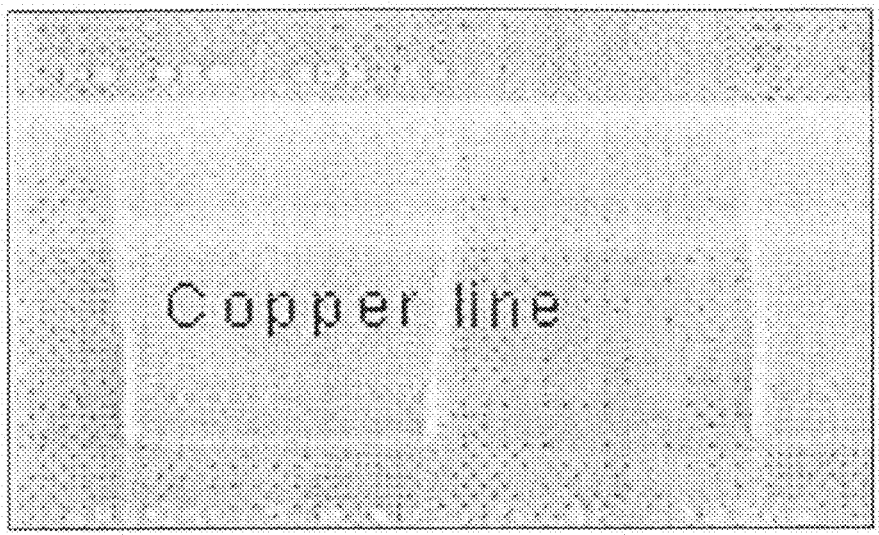
Figure 6D:
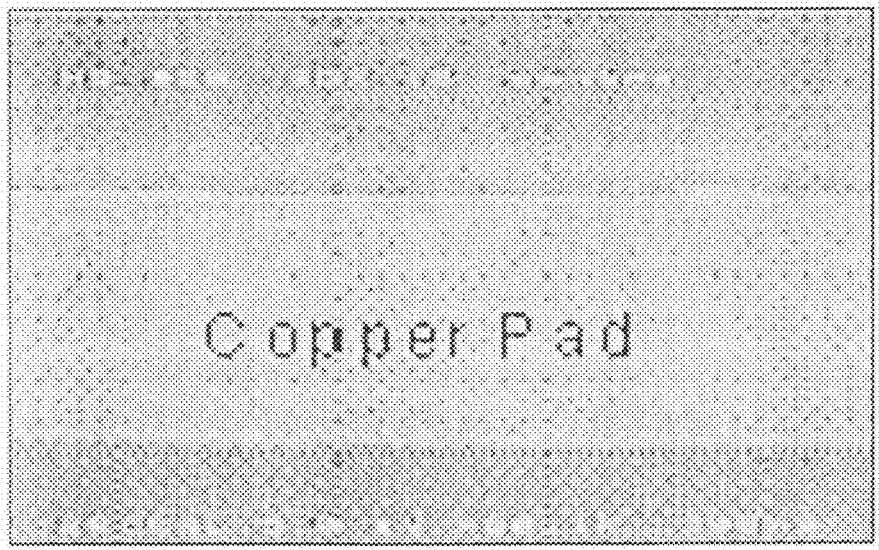

Here, the picosecond ultrasonics signals from an M6 wafer are compared with the corresponding cross sectional analysis as obtained by SEM. FIG. 6A represents the PSD (position sensitive detector) signal as recorded on a Cu 0.6 μm line array, while FIG. 6B shows the corresponding signal on a Cu full sheet box. In both cases, the well defined peak is used to calculate the thickness of the surface copper layer. FIG. 6C represents the SEM results corresponding to FIG. 6A for the Cu 0.6 μm line array, while FIG. 6D represents the SEM results corresponding to FIG. 6B for the Cu full sheet box.

Results from both techniques are summarized in Table 1 (where "PULSE" means that the system of FIGS. 3 and 4 was used to determine the Cu thickness):

TABLE 1

M6 level: Cu thickness.

| Structure/technique | Thickness/Å |
| --- | --- |
| Cu full sheet/PULSE | 6400 |
| Cu full sheet/SEM | 6396 |
| Cu line array/PULSE | 7688 |
| Cu line array/SEM | 7770 |

Figure 7:
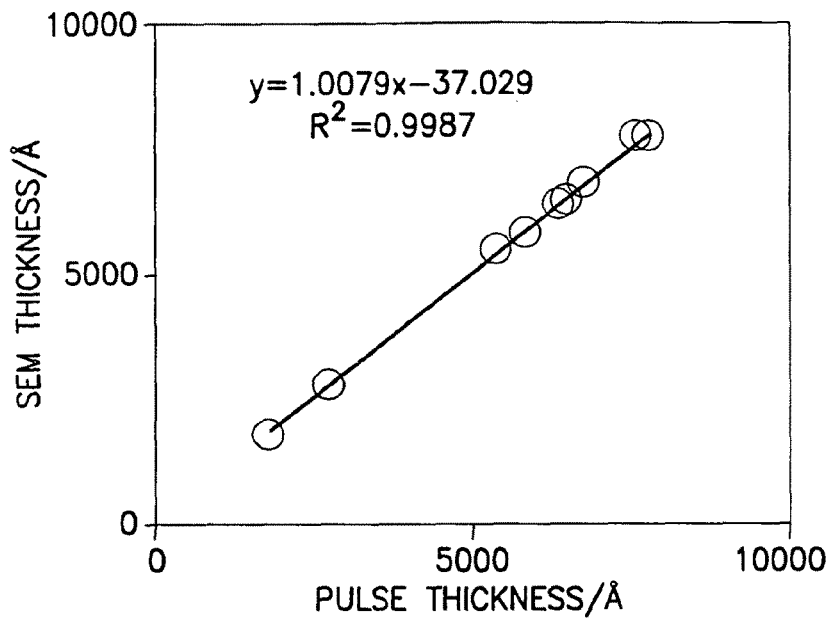
FIG. 7 shows a graph of correlation between SEM and PULSE thickness on PAD and Cu lines.

The correlation of SEM and PULSE thicknesses through all the range of thicknesses investigated is plotted in FIG. 7. Such accuracy of PULSE technique was obtained by assuming the velocity across copper being 48 Å/ps that is the typical expected sound velocity for a post CMP Cu material, whose crystal orientation is preferentially (1, 1, 1). See, e.g., C. Detavernier, D. Deduytsche, R. L. Van Meirhaeghe, J. De Baerdemaeker, C. Dauwe, "Room-temperature grain growth in sputter-deposited Cu films", Applied Physics Letters, v 82 (12), 24 Mar. 2003, 1863-5.

The measurement repeatability for the picosecond ultrasonic thickness results was tested on all metal levels, by performing each time a sequence of 15 static repeated measures. In addition, each wafer was loaded and unloaded ten times, and re-measured at the same die. The results are shown in Table 2.

TABLE 2

Repeatability and Reproducibility

| | Cu full sheet | | Cu line array | |
| --- | --- | --- | --- | --- |
| Metal | Static | Load/Unload | Static | Load/Unload |
| M1 | 0.53% | 0.55% | 0.34% | 0.44% |
| M2 | 0.41% | 0.60% | 0.28% | 0.30% |
| M3 | 0.39% | 0.51% | 0.32% | 0.41% |
| M4 | 0.48% | 0.62% | 0.47% | 0.45% |
| M5 | 0.47% | 0.53% | 0.51% | 0.50% |
| M6 | 0.22% | 0.81% | 0.19% | 0.32% |

Either in static or dynamic mode, the percent standard deviation of the results is within 0.8 percent, which demonstrates the technique is a robust control method.

Erosion & Dishing Application

Figure 8:
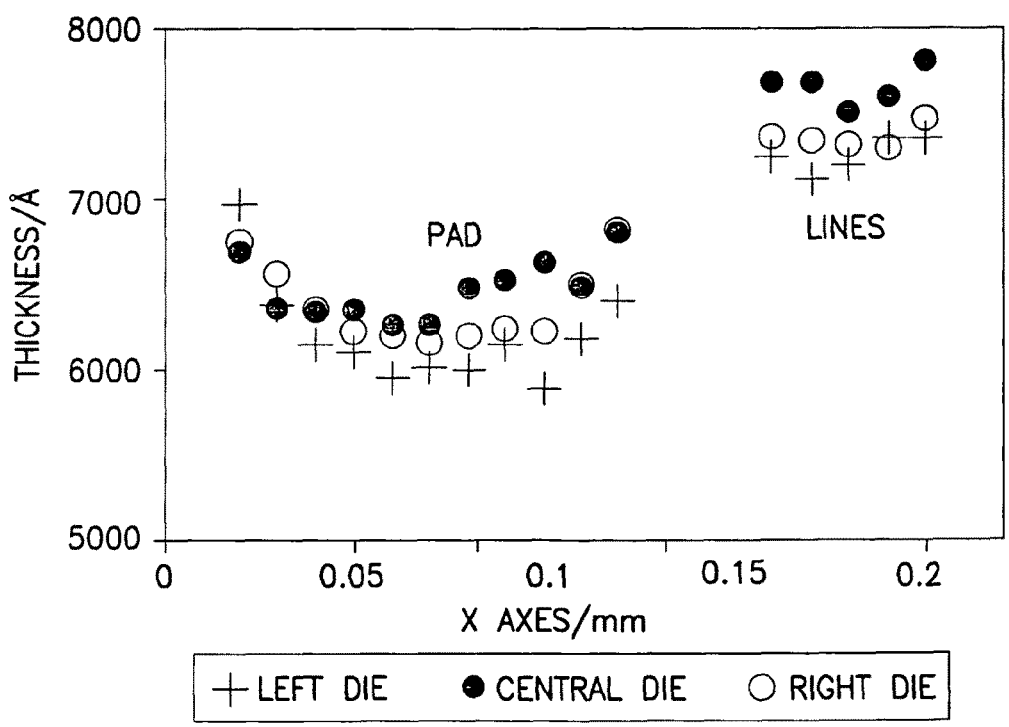
FIG. 8 shows a graph of thickness profile along X axes on Cu full sheet and line array boxes.

Dishing effects across the Cu pad and erosion on line arrays may result in residues in the next metal level. Metrology control is normally addressed by integrating Ellipsometry and High Resolution Profilometry (HRP), but the PULSE technique was demonstrated to be capable for metrology control (e.g., CMP control) as well. See C. Detavernier et al. above. Indeed, an Ellipsometer can only provide ILD thickness, and not Cu thickness, while HRP requires direct physical contact of a stylus to the wafer. This may result in contamination as well as physical damage to the wafer, which compromises the reliability and usability of this technique. The present PULSE technique can characterize the thickness profile through the Cu structure directly. For this purpose, a sequence of equal-separated sites was measured in the X direction across both Cu structures. A typical example is reported in FIG. 8.

In agreement with expectation, a Cu pad surrounded by ILD is polished thinner in the middle than at the edges, where the removal rate is the lowest. The same effect is also evident on line arrays, but here the variation of thickness is lower than on PAD because Cu lines are embedded in the ILD matrix.

Figure 9:
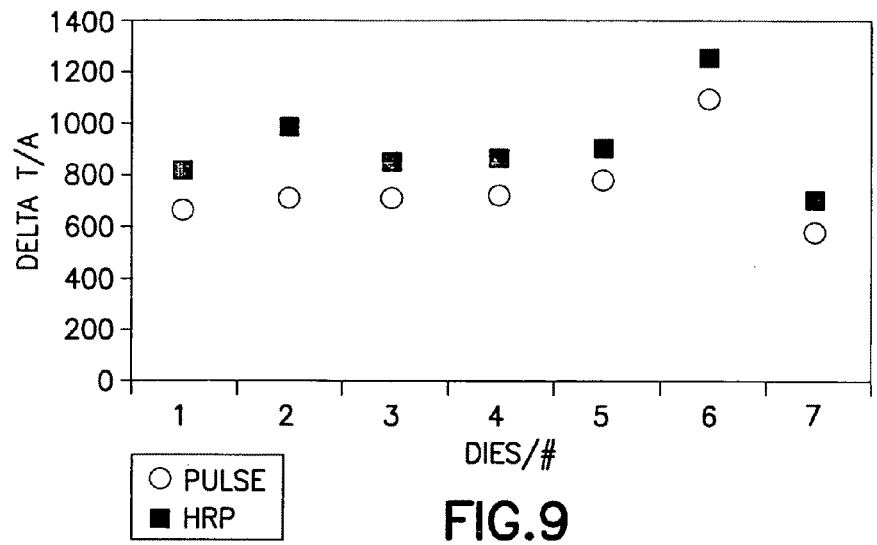
FIG. 9 shows a graph of maximum variation through the line, either in static or dynamic mode, the percent scans as measured by picosecond ultrasonics and High Resolution Profilometer across 7 dies.

To compare PULSE and HRP results, dishing profiles by MetaPULSE-II were repeated across the PAD structure on several dies. A quite important variation was reported, and, as depicted in FIG. 9, the ultrasonic result follows perfectly the trend reported by the HRP. The apparent underestimation by the picosecond ultrasonics is explainable with the different area scanned by the two techniques. In fact, HRP profile is performed by measuring from outside (ILD) to inside the full sheet Cu box, while MetaPULSE-II is measured only inside the Cu box, where more material is removed as compared with the ILD part.

Figure 10:
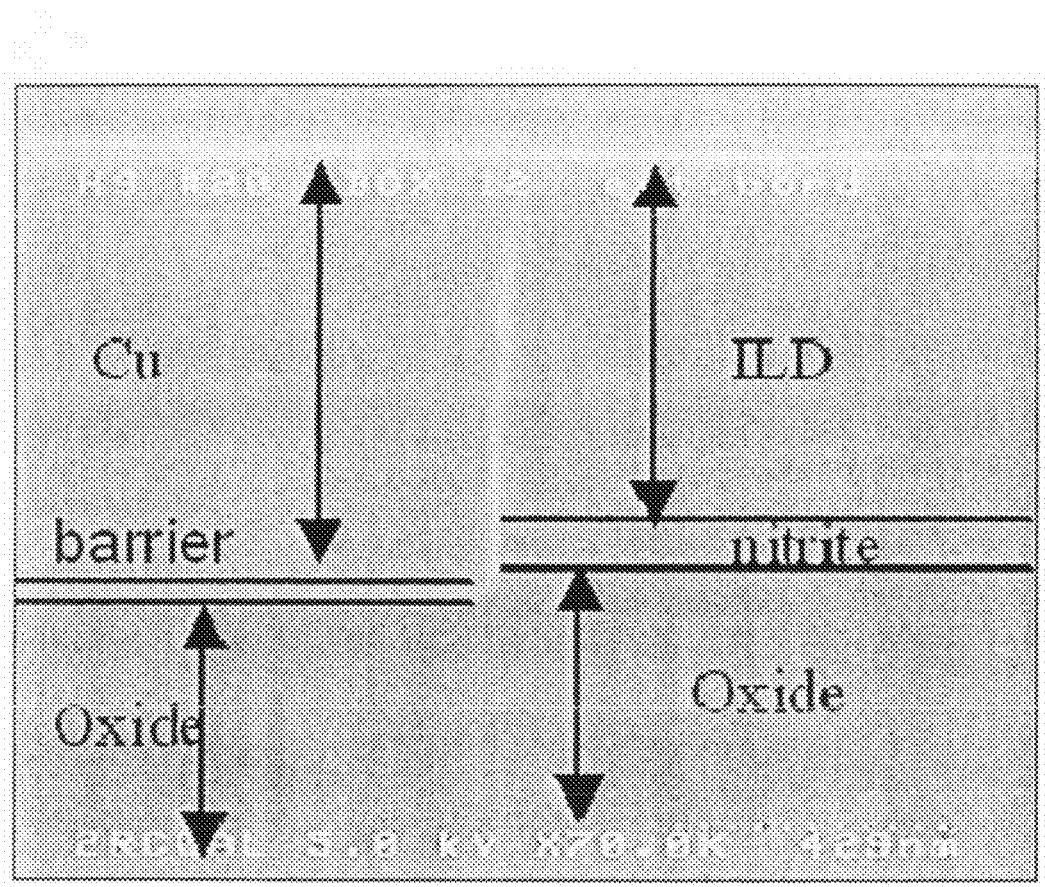
FIG. 10 shows stack composition by SEM: (left) inside Cu PAD, (right) outside Cu PAD.

Even though PULSE technique has been demonstrated as being capable of measuring ILD materials (see, e.g., L. Chapelon et al., "Using ultrasonics to measure the strength of porous ULK dielectrics", Solid State Technology, November 2006, 33-36), as a consequence of the CMP flow, the lower limit of the Cu layer has no common base line with the ILD stack. The evaluation of the erosion and dishing parameters, as they are defined, would require the measure of the oxide sitting below the copper layer. FIG. 10 shows the stack composition in a real case as seen by SEM.

Figure 11:
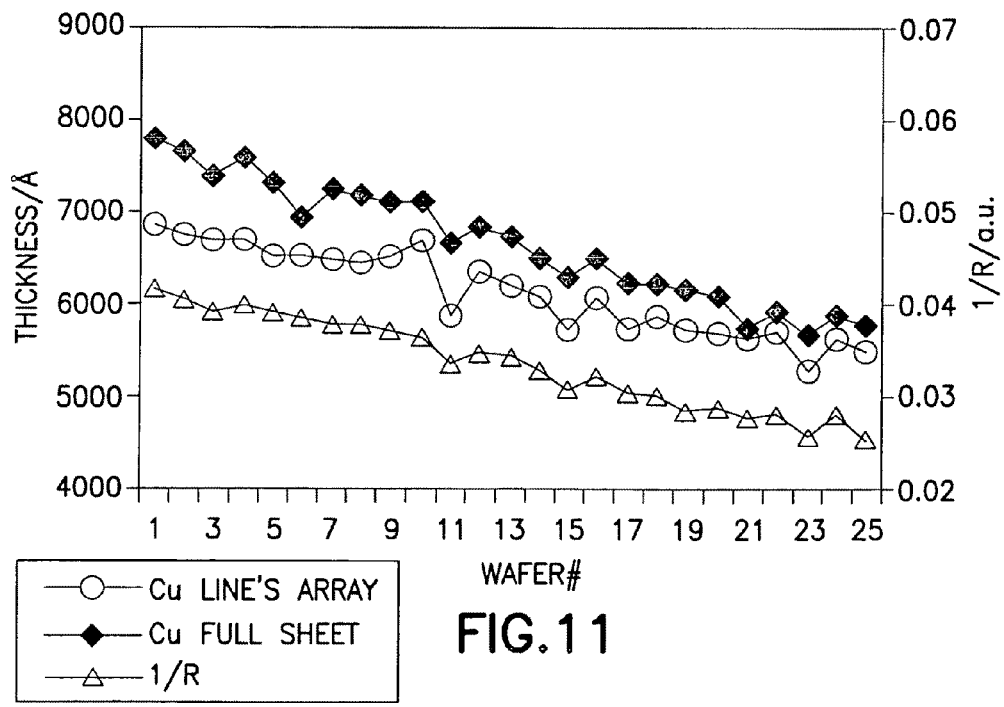
FIG. 11 shows a graph of Cu thickness of full sheet and line array, where CMP pressure was intentionally increased from wafer 1 to wafer 25.

However, measuring the absolute thickness on PAD and Cu lines is still enough to fully control the CMP process. As a case study, erosion on Cu lines and dishing across Cu pads were investigated herein through a set of M6 wafers processed with increasing CMP pressure. The thickness of full sheet and line arrays (0.6 μm in width) was measured by a MetaPULSE-II system on 9 dies/wafer. The average thicknesses and the corresponding sheet resistance of Cu lines are shown in FIG. 11 for all 25 wafers processed. Thickness results on full sheet and on line's array follow in general the same trend. As expected, copper lines resulted to be thicker that the corresponding full sheet. This is due to the fact that, in general, the near ILD exhibits the lowest removal rates and Cu the greatest removal rates. Consequently, more Cu is removed from the full sheet as compared with the line array. In addition, when considering the increasing pressure of the CMP process, more and more Cu material is removed from both full sheet and line arrays. Finally, the difference of thickness between full sheet and lines is decreasing, as the pressure applied by the CMP process is getting higher.

Remarkably, the thickness of line arrays is perfectly matching the inverse of sheet resistance. This result proves that the thickness parameter provided by the PULSE technique can be directly correlated with the final electrical performances.

IV. Characterizing Electroplated Copper on Various Line Structures

Figure 12A:
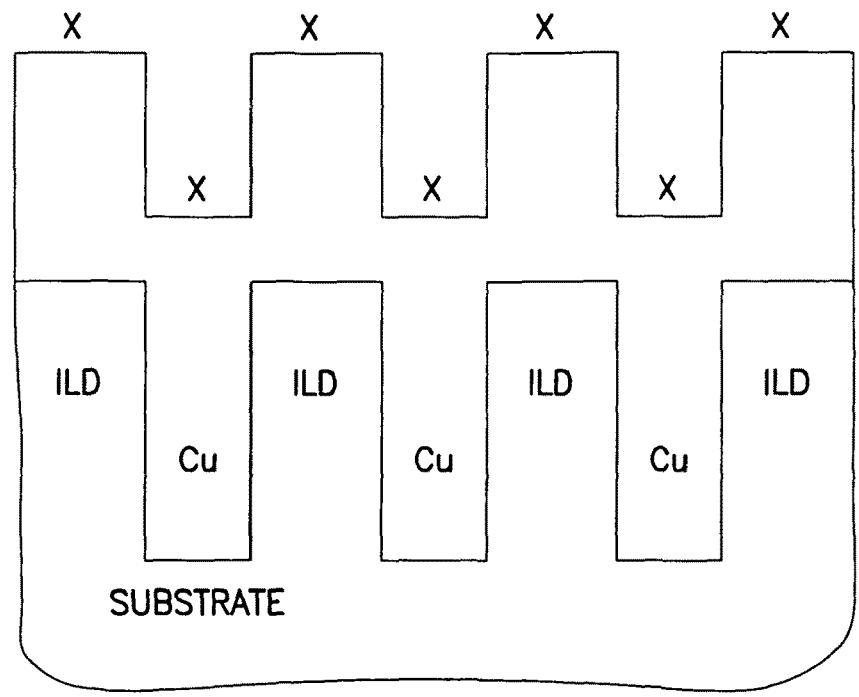
FIGS. 12A and 12B represent schematic sketches of ECP (electroplated) and partially polished structure (100 µm line width, 50 percent density), where X represents the measurement point.
Figure 12B:
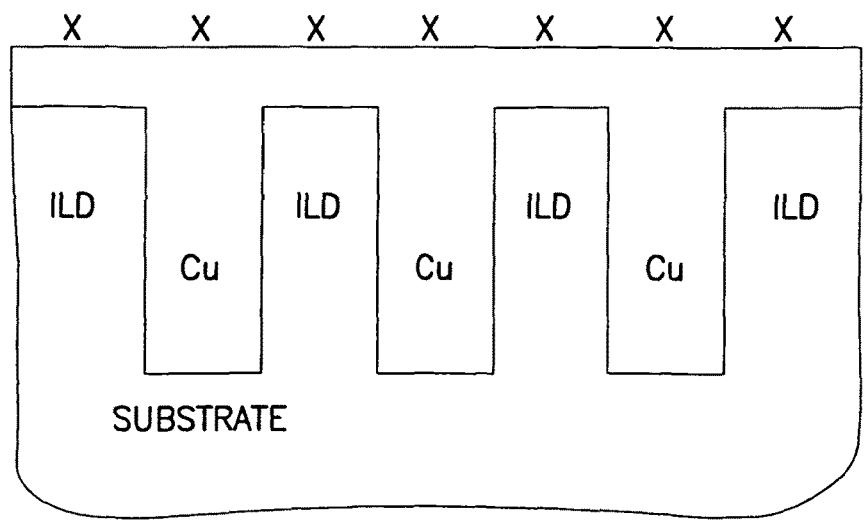

Picosecond ultrasonics is capable of measuring electroplated copper before CMP as well as on partially polished wafers. FIG. 12A shows a schematic sketch of wide line array (~100 μm width, 50 percent density) after electroplating, and the same structure after partial CMP is depicted in FIG. 12B. Line scan measurements were made across the structures covering the open field and the trenches on both wafers. The results are illustrated in FIGS. 12C and 12D respectively.

Figure 12C:
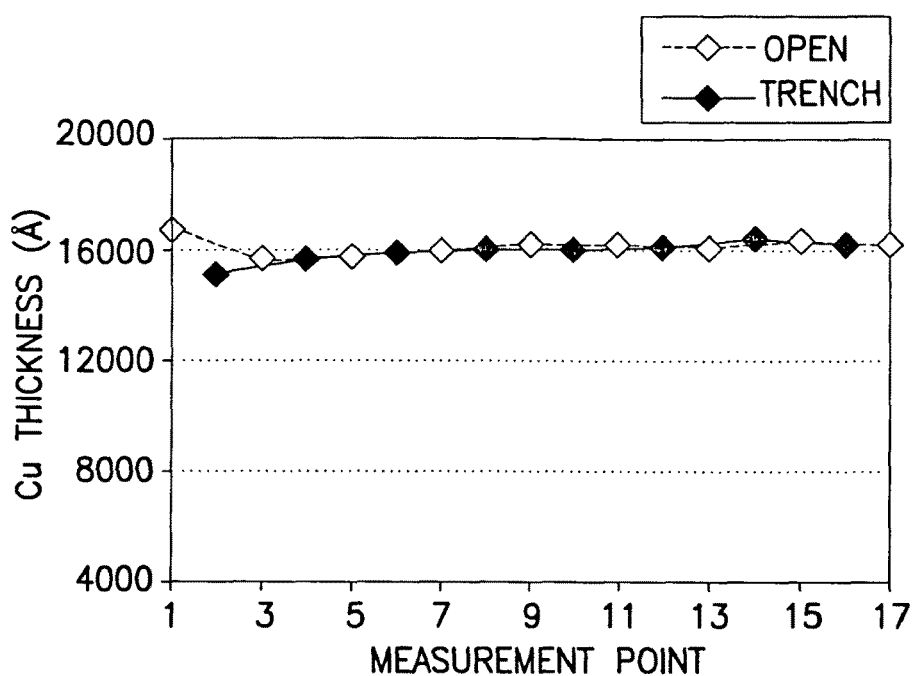
FIGS. 12C and 12D represent thickness profiles corresponding to FIGS. 12A and 12B, respectively.
Figure 12D:
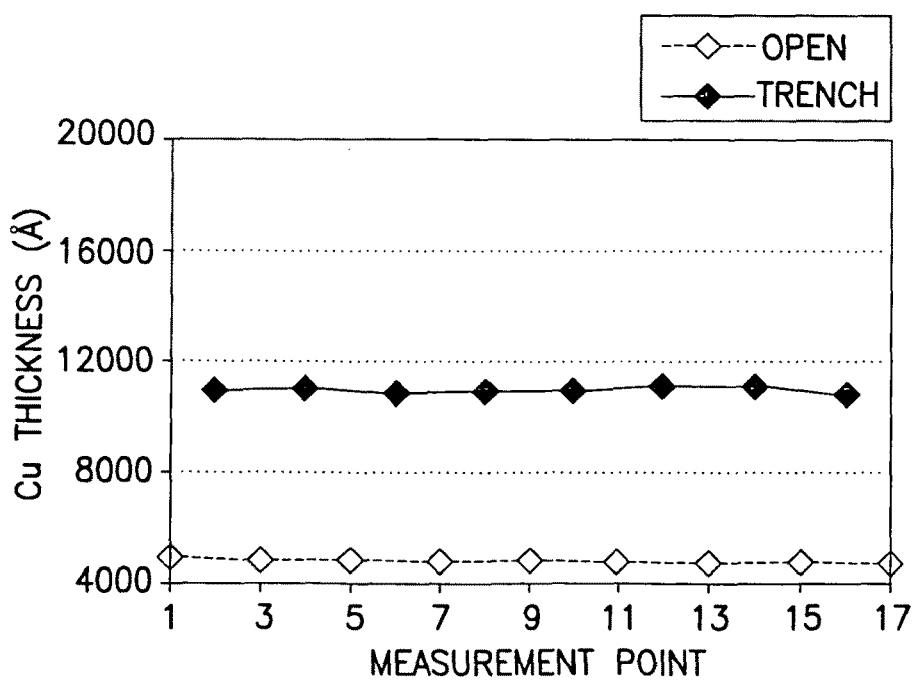

In FIG. 12C, after electroplating, the ECP (electroplated) Cu thickness is measured about 1.6 μm on both the open field and the trench structures. After partial CMP, the copper thickness in the open field region is about 4500 Å and in the trenches it is about 1.1 μm. Pattern dependent electroplating effects are readily seen. The time required for filling the wide trenches causes copper build-up in the open field areas hence the copper thickness is comparable from both the open field and trenches. However, on sub-micron line structures, copper build-up on top of the line arrays leads to "superfilling" of the lines. As a result, the copper in the trenches is thicker than the open field.

Figure 13A:
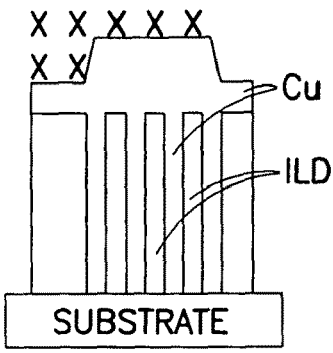
FIGS. 13A and 13B represent schematic sketches of post-ECP and partially polished line structure (0.25 µm line width, 50 percent density), where X represents the measurement point.
Figure 13B:
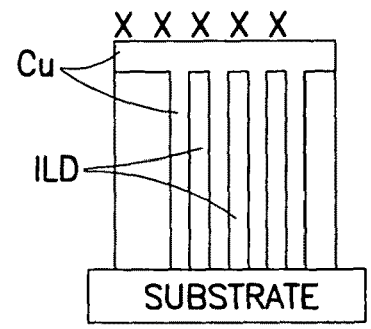
Figure 13C:
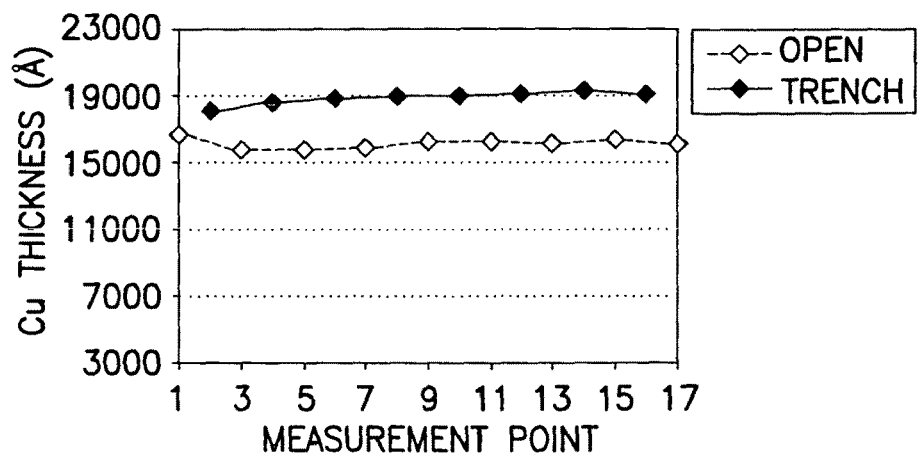
FIGS. 13C and 13D represent, corresponding to FIGS. 13A and 13B respectively, post-ECP and partially polished Cu thickness profiles.
Figure 13D:
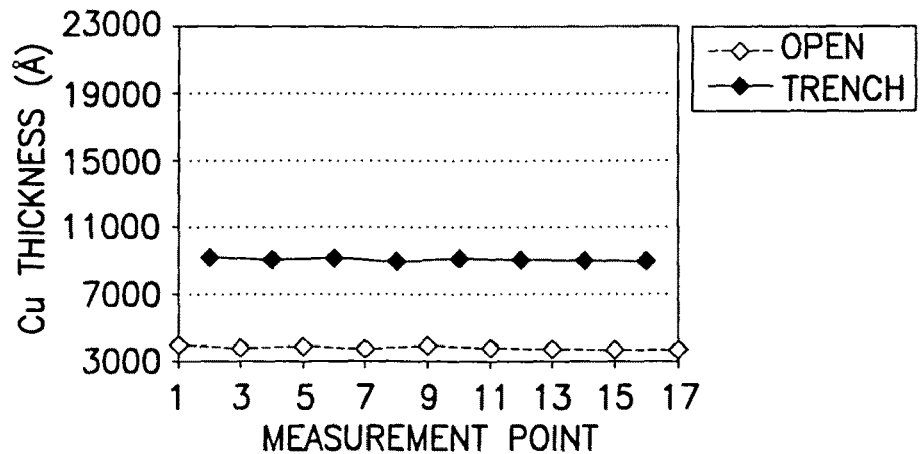

FIGS. 13A and 13B represent schematic sketches of post-ECP and partially polished line structure (0.25 μm line width, 50 percent density), where X represents the measurement. FIGS. 13C and 13D compare the measured Cu thickness between open field and sub-micron line areas on the pre-CMP wafer and partially polished wafer, respectively. As seen in FIG. 13C, due to superfilling of the trenches, the trench thickness (1.9 μm) is higher than the open field thickness (1.5 μm). After a partial CMP, the total thickness of trench plus the overburden is about 9000 Å compared to the open field thickness of 3800 Å.

Figure 14A:
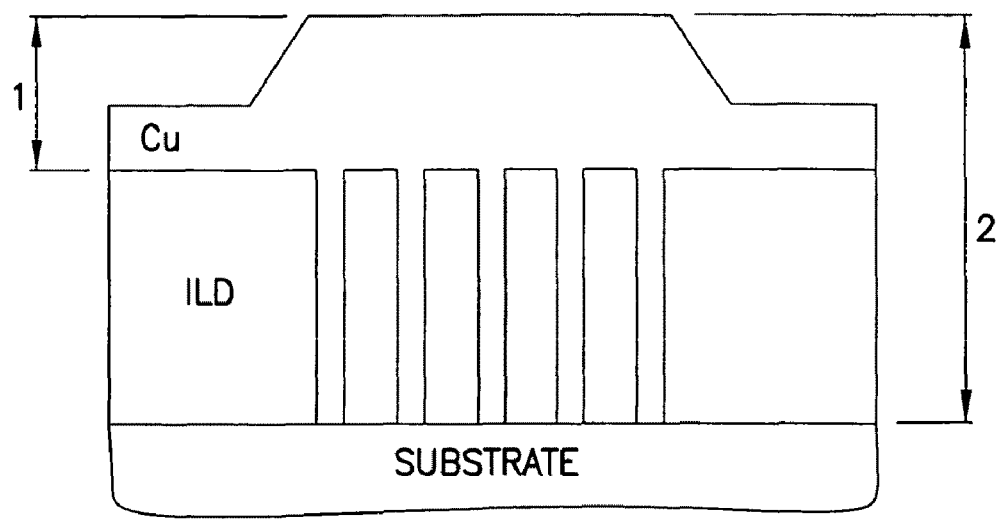
FIG. 14A represents raw data from a pre-CMP line array measurement, where echo 1 corresponds to the overburden thickness and echo 2 corresponds to the total thickness (line array+overburden)
Figure 14B:
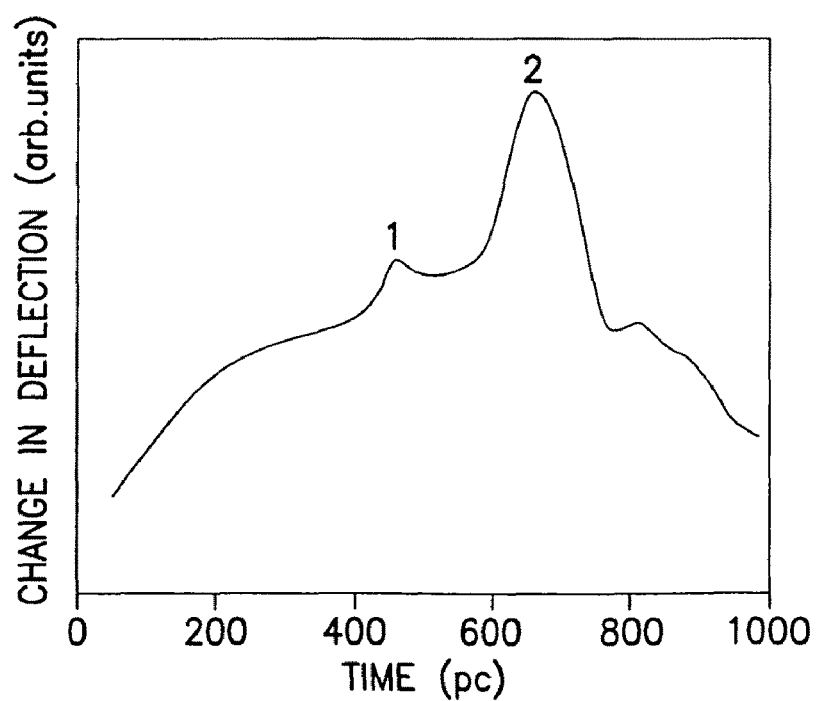
FIG. 14B corresponds to FIG. 14A and represents a schematic sketch of the cross-section of sub-micron line structures after electroplating and showing overburden and total thickness.

In FIG. 14A, an example of raw data from a pre-CMP line array structure (see FIG. 14B) is shown. The first echo, labeled as 1, appears at 450 ps and corresponds to thickness of copper overburden and the second echo, labeled as 2, at 680 ps corresponds to the total thickness of line array and over burden. Line array thickness is obtained from the time difference between the two echoes. Picosecond ultrasonic measurements from pre-CMP line structures, using the method and apparatus described above, have shown excellent correlation with the post-CMP thickness measurements and have been confirmed by using scanning electron microscopy (SEM).

Figure 15A:
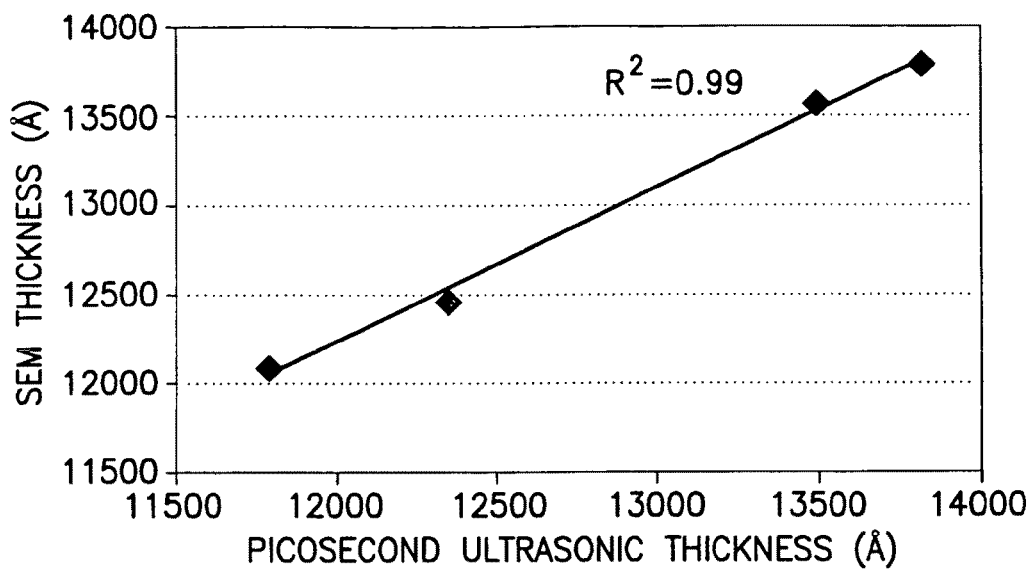
FIG. 15A is a graph representing picosecond ultrasonics versus SEM thickness correlation before CMP, where total thickness (line array+overburden) is shown, and where correlation is excellent with $R^2=0.99$.
Figure 15B:
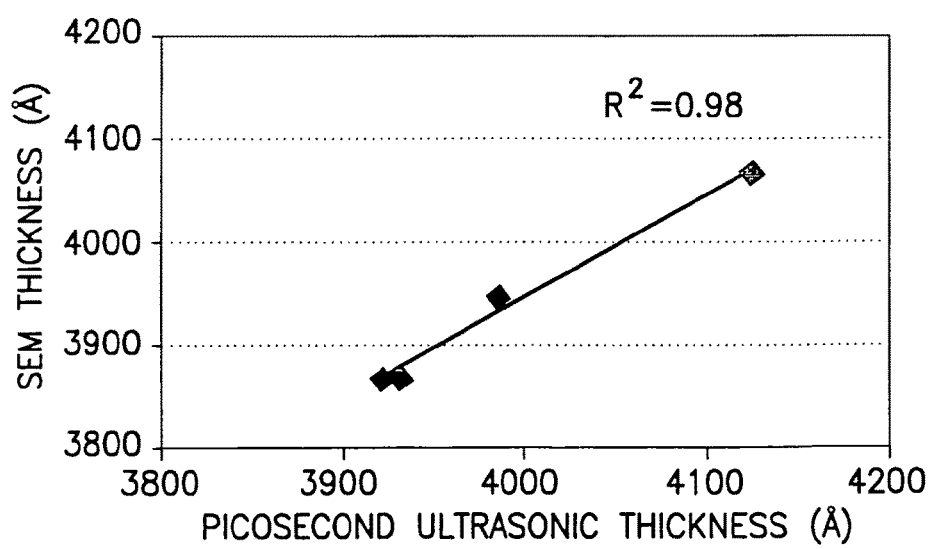
FIG. 15B is a graph representing post-CMP line array thickness, and this graph also shows excellent correlation between the two techniques.

Wafers having the same trench depth but plated to different target thicknesses were measured using picosecond ultrasonics. Pre-CMP measurements indicated that the Cu overburden is between 7500 Å and 9700 Å for the as-plated wafers, but the trench depth (array thickness) is about 4100 Å. Total thickness (copper overburden+line array) measurements from the picosecond ultrasonics showed excellent correlation with the total thickness numbers provided by the SEM measurements as seen in FIG. 15A. Duplicate sets of wafers were polished to compare the pre-CMP measurements with the post-CMP measurements. Post-CMP measurements of the line array showed excellent agreement with the pre-CMP array measurements as well as the SEM thickness (FIG. 15B). After CMP line array thickness was about 4000 Å. Data from 0.14 μm, 50 percent dense lines are summarized in the Table 1 below.

| Pre-CMP | | | | Post-CMP | |
| --- | --- | --- | --- | --- | --- |
| Ps Ultrasonics (A) | | | SEM (A) | Ps Ultrasonics (A) | SEM (A) |
| Cu overburden | Array Thickness | Total | Total | Array Thickness | Array Thickness |
| 9430 | 4062 | 13492 | 13571 | 3933 | 3869 |
| 9646 | 4174 | 13820 | 13790 | 3922 | 3869 |
| 7663 | 4128 | 11791 | 12083 | 3986 | 3948 |
| 7807 | 4541 | 12347 | 12461 | 4125 | 4064 |

Pre-CMP measurements such as these provide an opportunity for identifying potential process excursions and correcting them before the CMP step.

Characterizing Pattern-Dependent CMP

Figure 16:
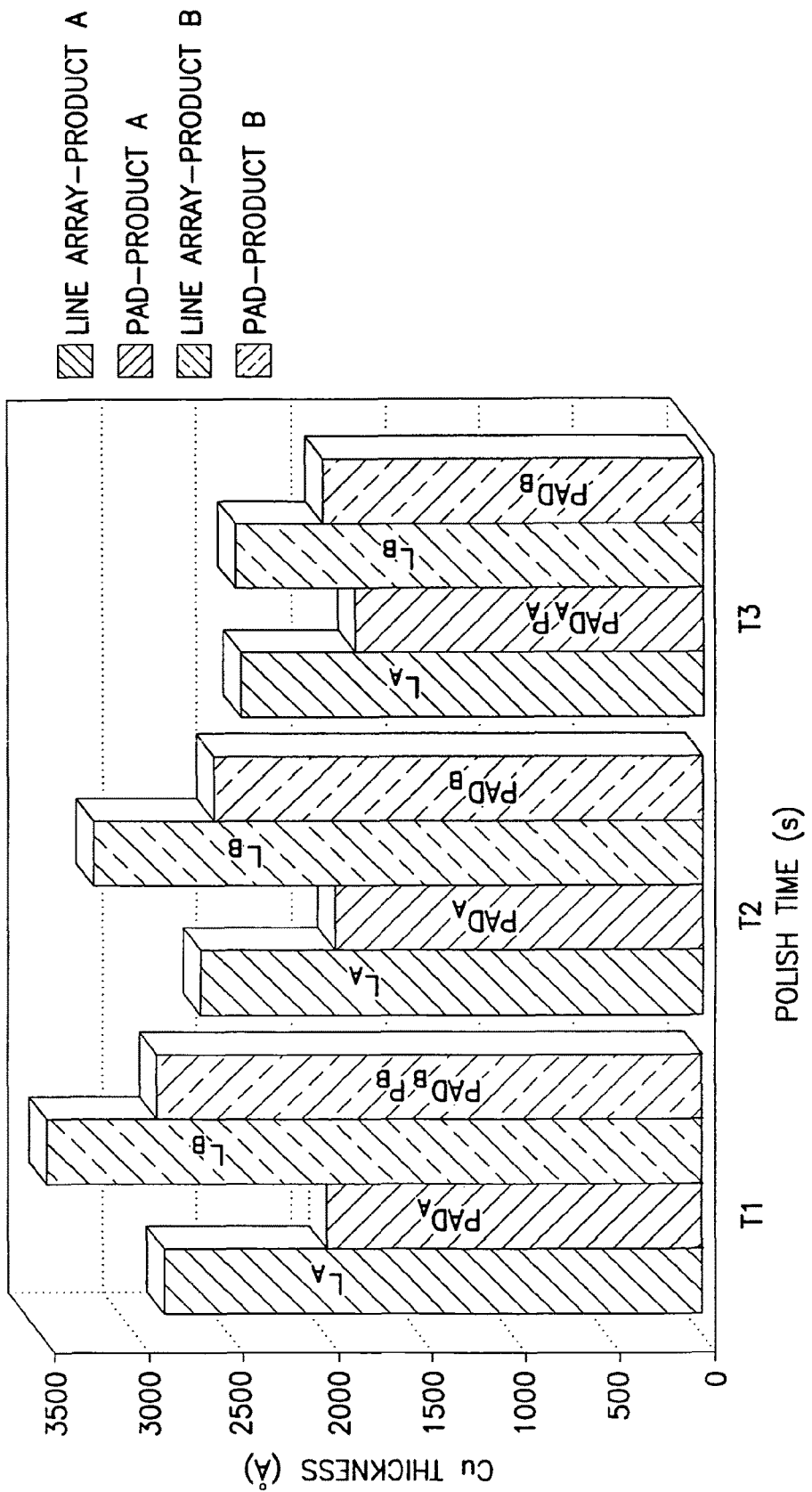
FIG. 16 is a graph illustrating effect of pattern-dependent CMP on products A and B having different die layout, where line array from product B ($L_B$) shows significant overburden after polishing for time T1, where additional polishing is required to reduce the over burden thickness, and where bond pads polish at a much faster rate than the line arrays for the same polishing time.

The effects of pattern-dependent CMP have been studied on two different products by polishing them for different times and measuring the remaining copper thickness using picosecond ultrasonics. FIG. 16 shows a plot of copper thickness versus CMP polishing times (T1<T2<T3) for the two products with different die layout; identified as A and B.

Line arrays (same width and density) and adjacent bond pads were selected for measurements. At time T1, line array on product B ($L_B$) shows significant overburden compared to that on product A ($L_A$). Additional polishing (times T2 and T3) is required to reduce the line thickness to within the process window for product B. At time T3, the line array thickness (2500 Å) from both the products are comparable and the optimal polishing time for each of the products was established.

Measurements from the bond pads are also shown for comparison. As expected the bond pads polish at a much faster rate than the line arrays. For product A, at time T1, the pad is 800 Å thinner than the line array. Bond pad on product A (Pad$_A$) also polishes at a faster rate than on B (Pad$_B$). This also demonstrates the need for measuring directly on line structures instead of monitoring the process by relying only on bond pad measurements. Using feedback provided by the picosecond ultrasonic measurements, the CMP process and polishing times were optimized for additional wafer processing.

Dishing and Erosion Measurements

Figure 17A:
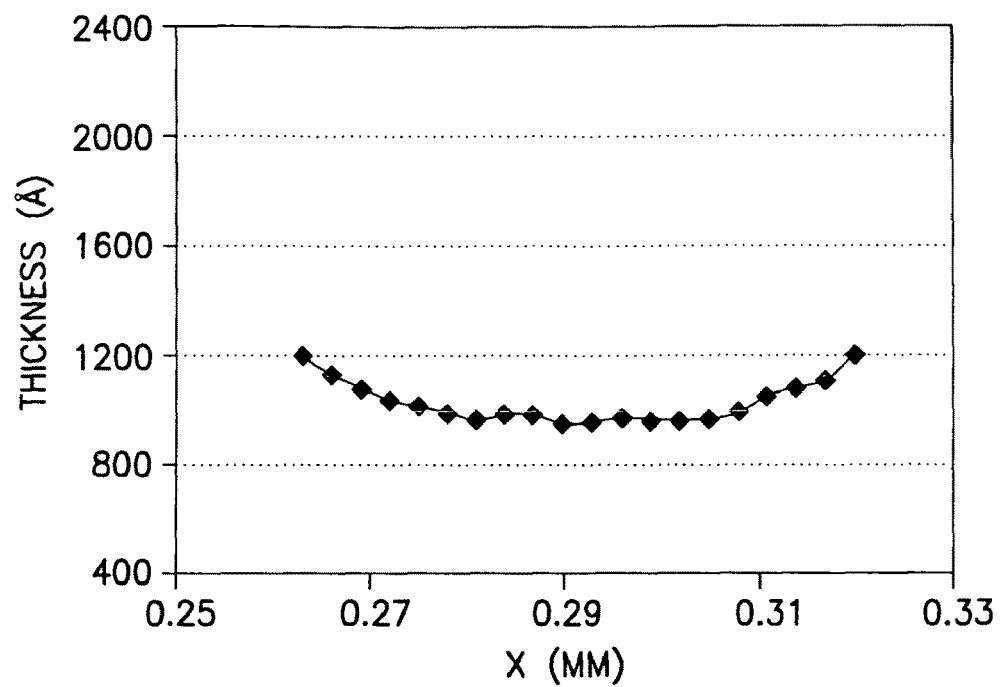
FIG. 17A is a graph illustrating high resolution (5 μm step) line scan measurements across a copper bond pad reveals the dishing across the structure, where copper thickness is ~900 Å at the center of the feature.
Figure 17B:
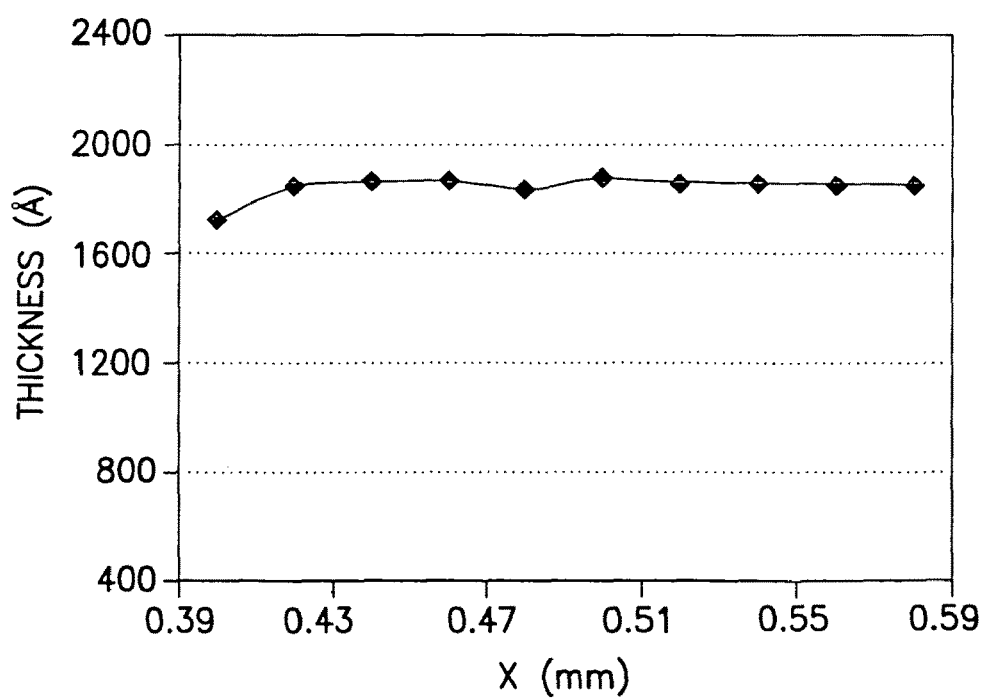
FIG. 17B is a graph illustrating high resolution line scan measurements across a sub-micron line array, where average copper thickness is ~1800 Å.

As seen in FIG. 16, bond pads polish more easily and also show extensive dishing compared to line arrays. FIGS. 17A and 17B show a high resolution line scan (5 µM step) across a 100 µm×100 µm bond pad and a similar scan across a sub-micron line structure for a center die. The bond pad is almost 50 percent thinner (~900 Å) than the line arrays (~1800 Å). If the process monitoring strategy relied only on bond pad measurements, it could lead to unnecessary scrapping of the wafer, although the copper thickness of the lines is well within the process tolerance range.

Figure 18A:
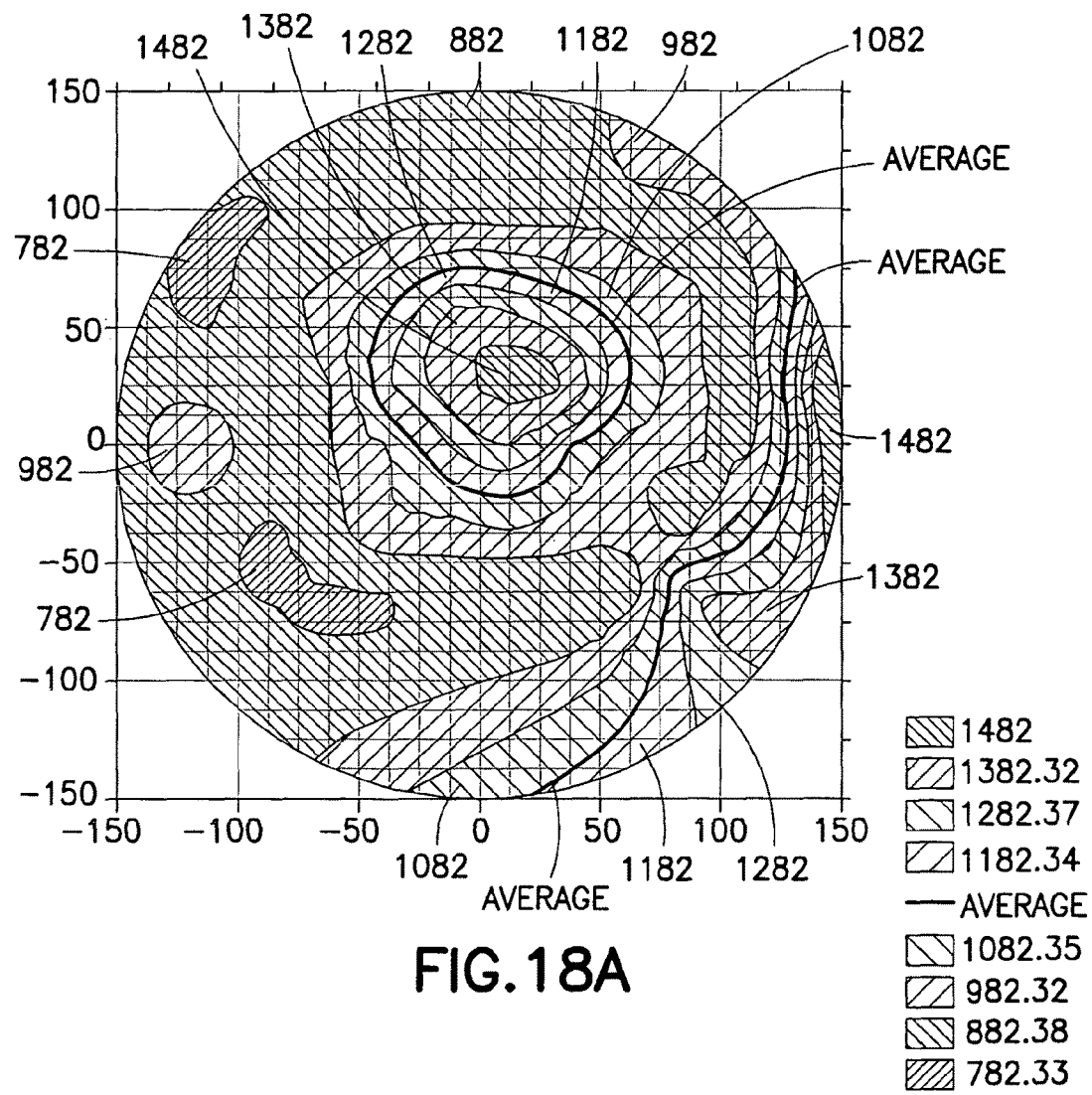
FIG. 18A is a within wafer uniformity profile of bond pad, where average thickness for the wafer is 980 Å.
Figure 18B:
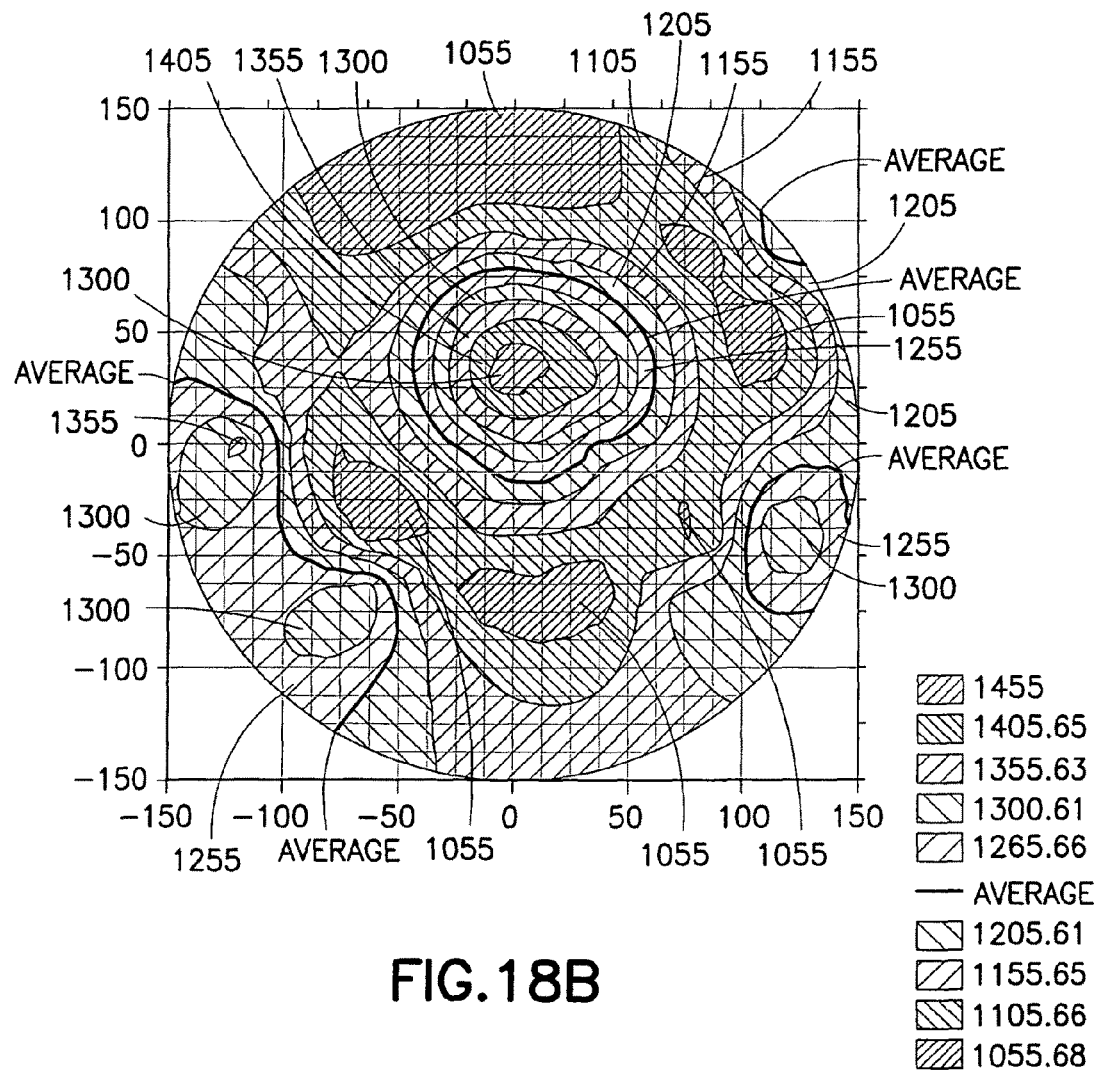
FIG. 18B is a within wafer uniformity profile of line array, where average thickness for the wafer is 1800 Å.

Within wafer uniformity maps to obtain the CMP profile are shown in FIGS. 18A and 18B for the bond pad and the line array respectively. Single point measurements were made at the center of the pad and the line array. The bond pad and line array show different CMP profiles. Bond pad is thicker at the center and at the right edge of the wafer. The line array profile shows the top edge die and the mid die are more easily polished than the center and the other edges.

Figure 19A:
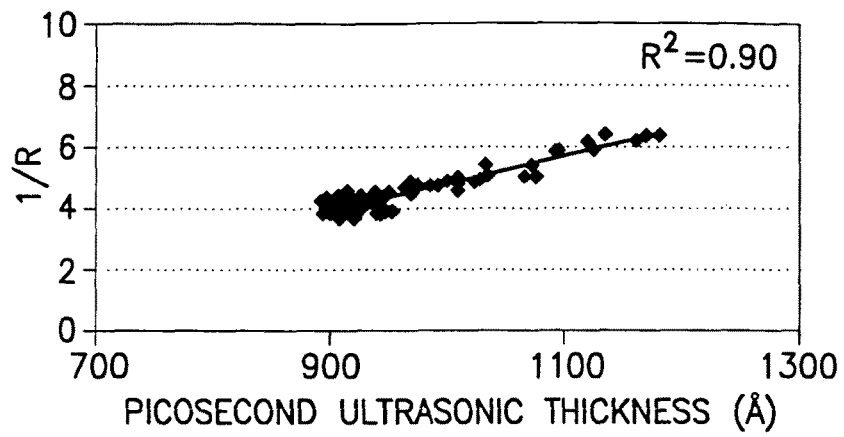
FIGS. 19A and 19B, illustrate that picosecond ultrasonic thickness versus electrical test data from 60 die measured on the wafer show excellent correlation, where
Figure 19B:
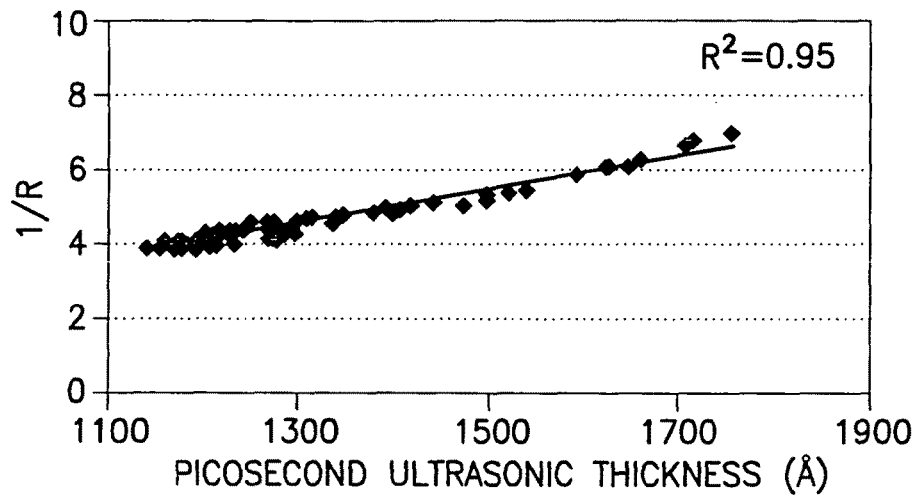

The wafer map measurements were compared with electrical tests from 60 dies measured on the wafer. FIGS. 19A and 19B show correlation of electrical test data for the bond pad and Cu line thickness, respectively. Excellent correlation ($R^2>0.9$) is obtained between the two techniques for both the pad and the line array. Such correlations with electrical test data are a requirement for making process control measurements on the line arrays especially at the 65 nm and below technology nodes. For high performance device operations, the lines should be maintained at the desired resistance to realize the high speed and low power requirements. Since it is not practical to use electrical measurements as an in-line process control, picosecond ultrasonics can be confidently adopted.

Figure 20:
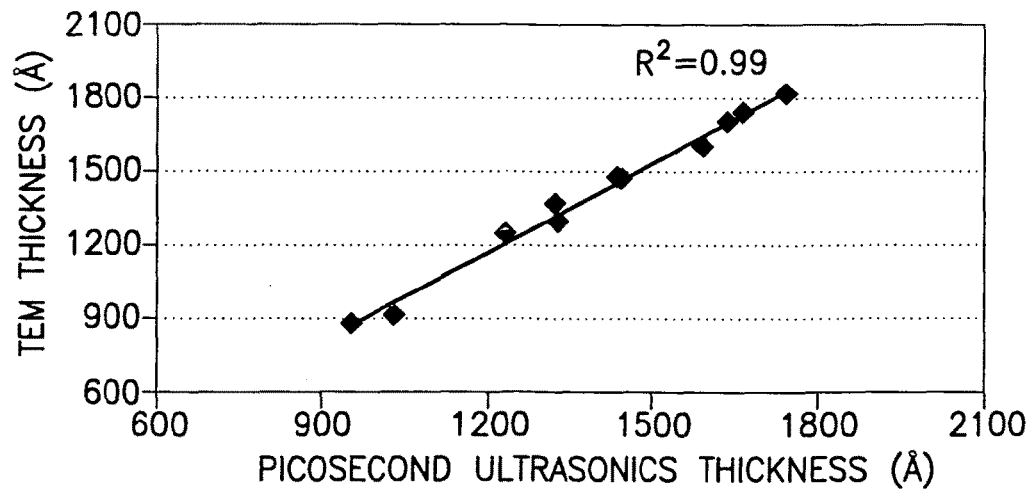
FIG. 20 is a graph illustrating picosecond ultrasonic measurements that show excellent correlation with TEM measurements for the line arrays.

Accuracy of the picosecond ultrasonic measurements on line arrays was also verified by correlating with TEM thickness. A total of 10 wafers covering a thickness range 900-1800 Å were measured using picosecond ultrasonics and the same dies were cross-sectioned to obtain TEM images. FIG. 20 shows the excellent correlation between the TEM and picosecond ultrasonics with an $R^2$ of 0.99.

Excursion Detection

Line array monitoring strategy using picosecond ultrasonic measurements are set up with an initial DOE (design-of-experiments) set of wafers that conforms to the process tolerance. Recipe development and optimization is carried out using these wafers and advanced modeling (EASy™). Die sampling on the wafers depends on the process maturity level. During initial development and process tuning, measurements are made across the entire wafer.

Figure 21A:
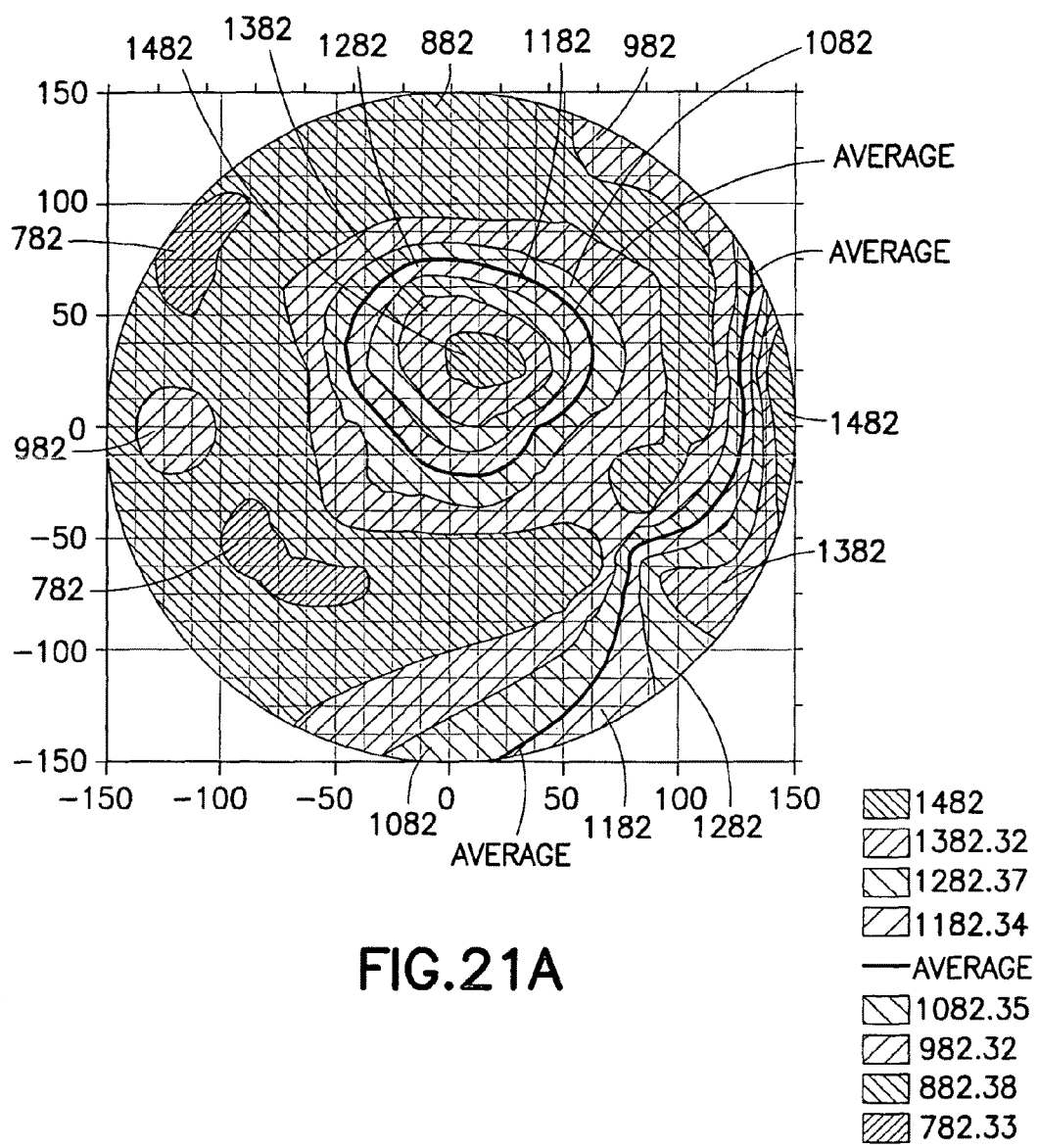
FIG. 21A illustrates within wafer uniformity profile of an over-polished wafer, where edge die thickness is about 800 Å compared to the wafer center (1400 Å)
Figure 21B:
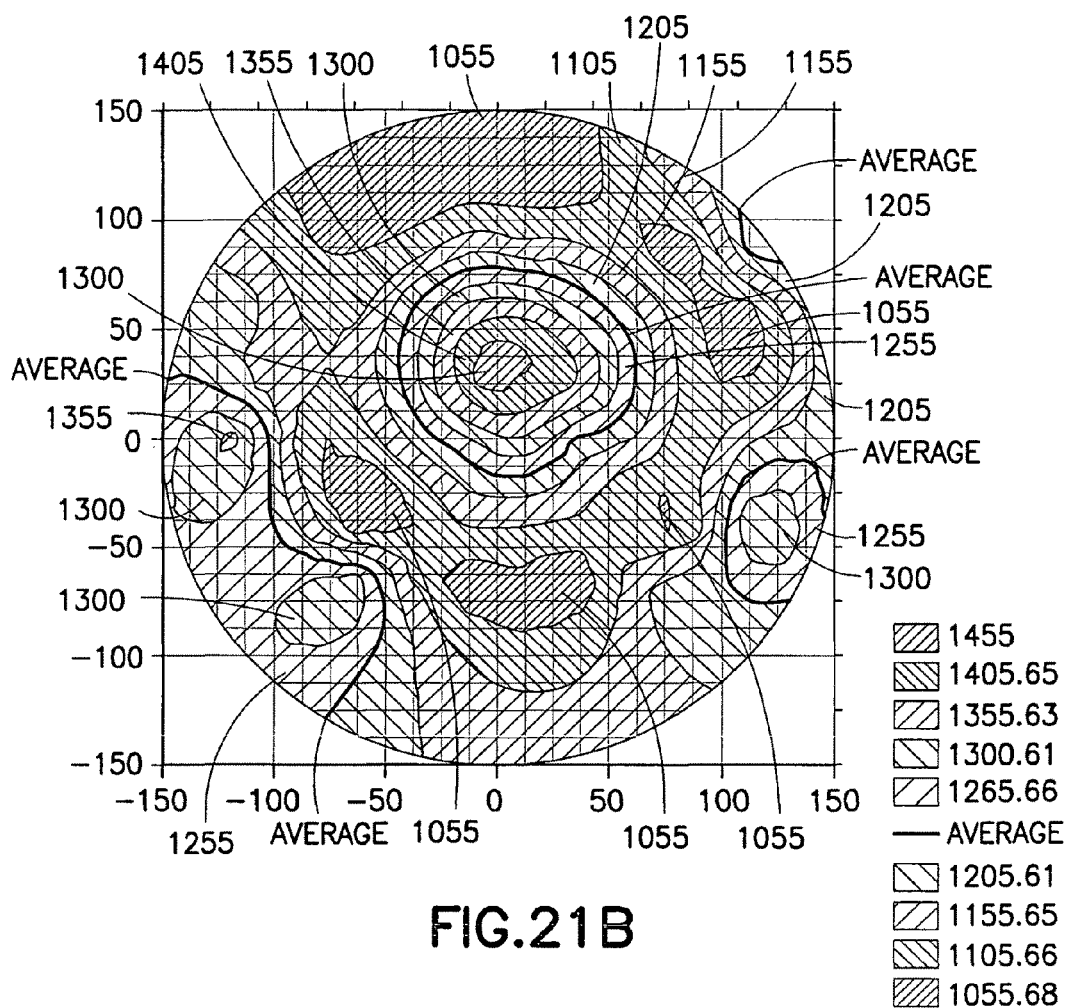
FIG. 21B illustrates within wafer uniformity profile after optimizing the polishing pressure, where variation between center (1400 Å) and edge dies (1100 Å) has improved.

Any misprocessing, such as over-polished wafer, under-polished wafer or presence of a residual layer are identified and flagged before transferring the wafers to subsequent process steps. Because of its small measurement size, picosecond ultrasonics is capable of measuring to the very edge of the wafer (1 mm from the edge), hence it provides a highly accurate within wafer uniformity. In FIG. 21A, within wafer uniformity profile from a wafer with over polished edge die is shown. During high pressure polishing, most of the edge dies on this wafer have been over polished (800 Å) compared to the wafer center (1400 Å). Data from a significantly improved process is also shown in FIG. 21B for comparison. Copper thickness at the center of the wafer ~1400 Å and the edge die ~1100 Å.

Edge Profile Application

In this application the attention is focused on the effect of the CMP process in proximity of the edge of the wafer. A structure of 10 µm width lines, with 5 µm of ILD between two lines, was characterized through the X and Y diameters (e.g., axes), where the Y axis passes through the wafer notch. Because of the product design, this structure is repeated very close to the edge of the wafer, e.g., the effect of the CMP process may be monitored on a single Cu line, as a function of the distance from the edge. On this line's structure, the measurement may extend up to 4 mm from the edge in the X direction, and to 7 mm in the Y direction being limited by the notch presence. Two wafers from different lots were measured.

Figure 22:
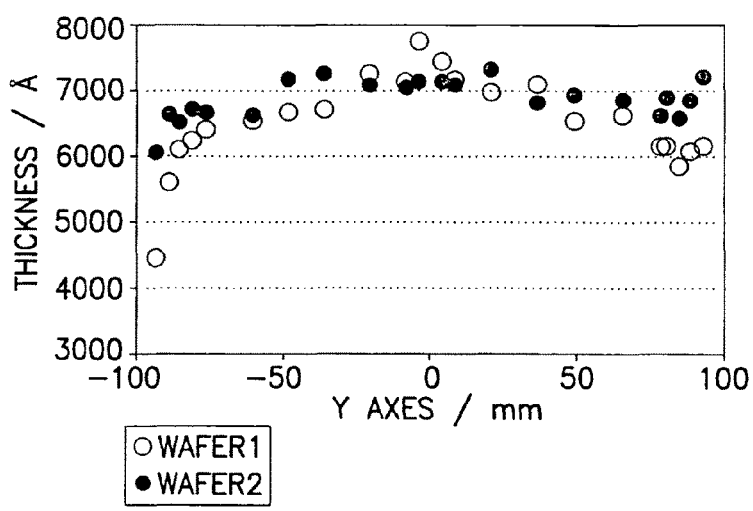
FIG. 22 shows a graph of Y diameter across a whole M6 product wafer, where edge exclusion is equal to 7 mm.

Across the X diameter, both wafers showed a huge reduction of Cu material while approaching the edge of the wafers (data not shown). The situation differs when looking at the Y direction (FIG. 22). In this case, the second measured wafer is definitely more flat than the first measured wafer. The reduction of thickness is only around 1000 Å from centre to edge, while in the previous case, the reduction was more than 3000 Å.

Perspectives

Picosecond Ultrasonics technique has been validated as a metrology solution for optimizing the CMP processing required by Dual-Damascene architectures. In particular, the capability of measuring Cu thickness of full sheet and line arrays in the sub-micron scale provides in turn a good control on the erosion and dishing effect. The methodology described has been tested extensively on several different products, and through all six metal levels required by the product flow.

In perspective, the Picosecond Ultrasonics investigation can be extended to the evaluation of mis-deposition of the starting Cu-electroplated by measuring the thickness of the Cu material inside and above the trench with one single measure before the CMP step.

The extendibility of these techniques down to the 45 nm node wafers has been demonstrated. Repeatability performance (1 sigma standard deviation) for line array measurements (for thickness <1000 A) is less than 0.5 percent and is well within the process control requirements.

The use of picosecond ultrasonics have been described for monitoring electroplated copper and CMP processes on both line arrays and solid pads. The technique can be adopted for automated process control to provide feedback, feed-forward information for electroplating and CMP processes. Accuracy of this method has shown excellent correlation with both SEM and TEM. An excellent correlation with electrical test data, which is important for process control, has also been demonstrated. Since the technique is not sensitive to underlying layers, measurements can be made directly on structures for all metallization levels (M1-M8). Measurements can be made rapidly providing a strategy for monitoring the process at both the die-level and wafer-level which will be a requirement at the future technology nodes. Extendibility of this technique to the 45 nm node has also been demonstrated with promising results.

Additionally, the techniques described may be used for automated defect categorization. Characteristics of the sample IC may be determined. These features may be evaluated to determine if the manufacturing process resulted in a defective IC. Furthermore, the individual IC may be evaluated to determine whether it may be salvaged, e.g., through additional process steps, or if the IC must be scraped.

Figure 23:
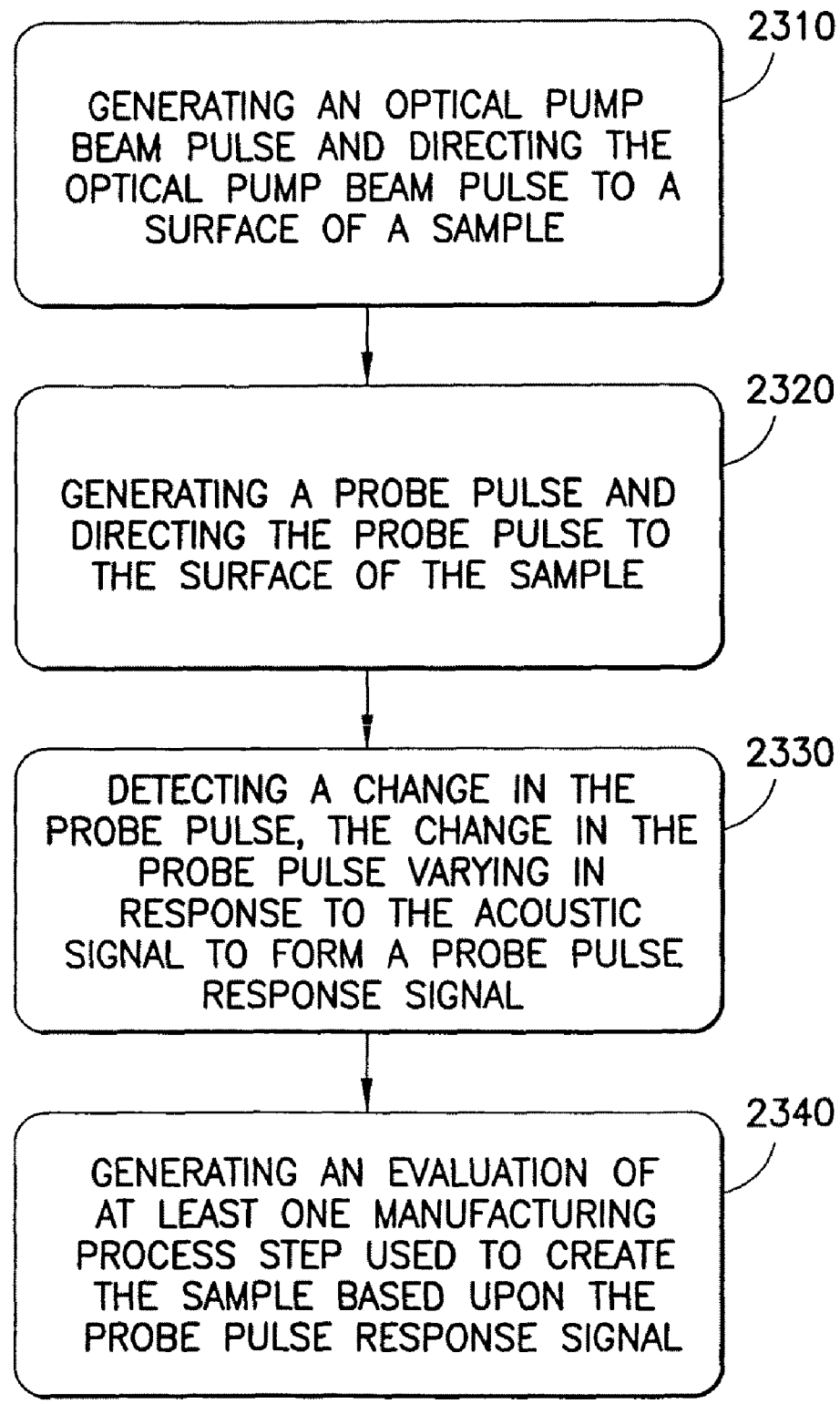
FIG. 23 illustrates a simplified flow diagram of a method for evaluating a manufacturing process.

FIG. 23 illustrates a simplified flow diagram of a exemplary method in accordance with this invention for evaluating a manufacturing process. An optical pump beam pulse is generated and directed the optical pump beam pulse to a surface of a sample, in block 2310. In block 2320, a probe pulse is generated and directed the probe pulse to the surface of the sample. In block 2330, a probe pulse response signal is detected. A change in the probe pulse varying in response to the acoustic signal forms the probe pulse response signal. An evaluation of at least one manufacturing process step used to create the sample is made based upon the probe pulse response signal, in block 2340.

An exemplary embodiment in accordance with this invention is a method for evaluating a manufacturing process. The method includes generating an optical pump beam pulse and directing the optical pump beam pulse to a surface of a sample. A probe pulse is generated and directed the probe pulse to the surface of the sample. A probe pulse response signal is detected. A change in the probe pulse varying in response to the acoustic signal forms the probe pulse response signal. An evaluation of one or more manufacturing process steps used to create the sample is made based upon the probe pulse response signal.

In a further exemplary embodiment of the method above, generating the evaluation includes associating the probe pulse response signal with one or more characteristics of the sample, and generating the evaluation of the one or more manufacturing process steps is based upon the one or more characteristics of the sample. The one or more characteristics may be a thickness of a dielectric pad, a thickness of a copper pad, or a thickness of a line array. Additionally, the evaluation may include determining whether the one or more manufacturing process steps are producing the one or more characteristics of the sample within an acceptable tolerance.

In another exemplary embodiment of any of the methods above, the manufacturing process is a chemical mechanical planerization process.

In a further exemplary embodiment of any of the methods above, the methods include generating the sample using a first manufacturing process. The methods may also include automatically adjusting the first manufacturing process based upon the evaluation of the one or more manufacturing process step to create a second manufacturing process. The adjusting may include adding one or more remediation process steps to the first manufacturing process and/or modifying normal process parameters of one or more manufacturing steps in the first manufacturing process.

In another exemplary embodiment of any of the methods above, the methods include ceasing production of one or more other sample based upon the evaluation of the one or more manufacturing process.

In a further exemplary embodiment of any of the methods above, the evaluation of the one or more manufacturing process steps includes determining whether the one or more manufacturing process steps result in generating a sample that satisfies one or more desired substrate characteristics.

In another exemplary embodiment of any of the methods above, detecting a change in the probe pulse includes detecting a deflection of the probe pulse and/or detecting a change in reflectance of the sample.

In a further exemplary embodiment of any of the methods above, the methods are performed as a result of execution of computer program instructions stored in a computer readable memory medium.

Another exemplary embodiment in accordance with this invention is an apparatus for evaluating a manufacturing process. The apparatus includes a light source configured to generate an optical pump beam pulse, to direct the optical pump beam pulse to a surface of a sample to generate an acoustic signal, to generate a probe pulse and to direct the probe pulse to the surface of the sample. A detector is included to detect a probe pulse response signal. The probe pulse response signal is formed based on a change in the probe pulse varying in response to the acoustic signal. A processing unit, which can generate an evaluation of one or more manufacturing process steps of a first manufacturing process used to create the sample based upon the probe pulse response signal, is also included.

In a further exemplary embodiment of the apparatus above, the processing unit can also associate the probe pulse response signal with one or more characteristics of the sample; and generate the evaluation based upon the one or more characteristics of the sample. The one or more characteristics may be a thickness of a dielectric pad, a thickness of a copper pad, or a thickness of a line array.

In another exemplary embodiment of any of the apparatus above, the processing unit can also automatically adjust the first manufacturing process based upon the evaluation of the at least one manufacturing process step to create a second manufacturing process.

In a further exemplary embodiment of any of the apparatus above, the detector can detect a deflection of the probe pulse and/or a change in reflectance of the sample.

Another exemplary embodiment in accordance with this invention is an apparatus for evaluating a manufacturing process. The apparatus includes a first means for generating an optical pump beam pulse and directing the optical pump beam pulse to a surface of a sample. A second means for generating a probe pulse and directing the probe pulse to the surface of the sample is included. The apparatus includes a means for detecting a probe pulse response signal. A change in the probe pulse varying in response to the acoustic signal forms the probe pulse response signal. An evaluation means for generating an evaluation of at least one manufacturing process step used to create the sample based upon the probe pulse response signal is included.

In a further exemplary embodiment of the apparatus above, the first generating means is a pulsed laser, the second generating means is the pulsed laser, the detecting means is a detector, and the evaluation means is a processing unit.

The foregoing description has provided by way of exemplary and non-limiting examples a full and informative description of the best techniques presently contemplated by the inventors for carrying out embodiments of the invention. However, various modifications and adaptations may become apparent to those skilled in the relevant arts in view of the foregoing description, when read in conjunction with the accompanying drawings and the appended claims. All such and similar modifications of the teachings of this invention will still fall within the scope of this invention.

Furthermore, some of the features of exemplary embodiments of this invention could be used to advantage without the corresponding use of other features. As such, the foregoing description should be considered as merely illustrative of the principles of embodiments of the present invention, and not in limitation thereof.

What is claimed is:

1. A method comprising:
generating an optical pump beam pulse and directing the optical pump beam pulse to a surface of a sample to generate an acoustic signal, where the sample comprises a line array and an overburden;
generating a probe pulse and directing the probe pulse to the surface of the sample;
detecting a probe pulse response signal, where a change in the probe pulse varying in response to the acoustic signal forms the probe pulse response signal, where the probe pulse response signal comprises an indication of a first echo and a second echo;

determining a characteristic of a line array based at least in part on the first echo and the second echo; and generating an evaluation of at least one manufacturing process step used to create the sample based upon the characteristic of the line array.

2. The method of claim 1, where the evaluation comprises a determination of whether the at least one manufacturing process step is producing the line array within an acceptable tolerance.

3. The method of claim 1, where the manufacturing process is a chemical mechanical planerization process.

4. The method of claim 1, further comprising generating the sample using a first manufacturing process.

5. The method of claim 4, further comprising automatically adjusting the first manufacturing process based upon the evaluation of the at least one manufacturing process step to create a second manufacturing process.

6. The method of claim 5, where the adjusting comprises adding at least one remediation process step to the first manufacturing process.

7. The method of claim 5, where the adjusting comprises modifying normal process parameters of at least one manufacturing step that comprises a part of the first manufacturing process.

8. The method of claim 1, further comprising ceasing production of at least one other sample based upon the evaluation of the at least one manufacturing process.

9. The method of claim 1, where the evaluation of the at least one manufacturing process step comprises determining whether the at least one manufacturing process step results in generating a sample that satisfies at least one desired substrate characteristic.

10. The method of claim 1, where detecting a change in the probe pulse comprises at least one of detecting a deflection of the probe pulse and detecting a change in reflectance of the sample.

11. The method of claim 1, where the method is performed as a result of execution of computer program instructions stored in a computer readable memory medium.

12. An apparatus comprising:

a light source configured:

to generate an optical pump beam pulse, to direct the optical pump beam pulse to a surface of a sample to generate an acoustic signal, where the sample comprises a line array and an overburden, to generate a probe pulse and to direct the probe pulse to the surface of the sample;

a detector configured to detect a probe pulse response signal, where the probe pulse response signal is formed based on a change in the probe pulse varying in response to the acoustic signal, where the probe pulse response signal comprises an indication of a first echo and a second echo; and a processing unit configured to determine a characteristic of a line array based at least in part on the first echo and the second echo and configured to generate an evaluation of at least one manufacturing process step of a first manufacturing process used to create the sample based upon the characteristic of the line array.

13. The apparatus of claim 12, where the processing unit is further configured to automatically adjust the first manufacturing process based upon the evaluation of the at least one manufacturing process step to create a second manufacturing process.

14. The apparatus of claim 12, where the detector is configured to detect at least one of a deflection of the probe pulse and a change in reflectance of the sample.

15. An apparatus comprising:

first means for generating an optical pump beam pulse and directing the optical pump beam pulse to a surface of a sample to generate an acoustic signal, where the sample comprises a line array and an overburden;

second means for generating a probe pulse and directing the probe pulse to the surface of the sample;

means for detecting a probe pulse response signal, where a change in the probe pulse varying in response to the acoustic signal forms the probe pulse response signal, where the probe pulse response signal comprises an indication of a first echo and a second echo;

means for determining a characteristic of a line array based at least in part on the first echo and the second echo; and evaluation means for generating an evaluation of at least one manufacturing process step used to create the sample based upon the characteristic of the line array.

16. The apparatus of claim 15, where the first generating means is a pulsed laser, the second generating means is the pulsed laser, the detecting means is a detector, and the evaluation means is a processing unit.

17. The method of claim 1, where first echo corresponds to an echo of signal passing through a thickness of the overburden and the second echo corresponds to an echo of the signal passing through a combined thickness of the line array and the overburden.

18. The method of claim 17, where determining the characteristic of a line array is based on a time difference between the first echo and the second echo.

19. The apparatus of claim 12, where first echo corresponds to an echo of signal passing through a characteristic of the overburden and the second echo corresponds to an echo of the signal passing through a characteristic of the line array and the overburden.

20. The apparatus of claim 19, where determining the characteristic of a line array is based on a time difference between the first echo and the second echo.

* * * * *